(12) United States Patent
Gyoten et al.

(10) Patent No.: US 11,364,327 B2
(45) Date of Patent: Jun. 21, 2022

(54) HEAT EXCHANGER, OXYGENATOR, AND METHOD OF MANUFACTURING A HEAT EXCHANGER

(71) Applicant: TERUMO KABUSHIKI KAISHA, Tokyo (JP)

(72) Inventors: Akira Gyoten, Elkton, MD (US); Ryuji Hiraguchi, Elkton, MD (US)

(73) Assignee: TERUMO KABUSHIKI KAISHA, Tokyo (JP)

( * ) Notice: Subject to any disclaimer, the term of this patent is extended or adjusted under 35 U.S.C. 154(b) by 733 days.

(21) Appl. No.: 16/273,495

(22) Filed: Feb. 12, 2019

(65) Prior Publication Data

US 2019/0175811 A1 Jun. 13, 2019

Related U.S. Application Data

(63) Continuation of application No. PCT/JP2017/030332, filed on Aug. 24, 2017.

(30) Foreign Application Priority Data

Aug. 31, 2016 (JP) .............................. JP2016-169931

(51) Int. Cl.
*A61M 1/16* (2006.01)
*B01D 63/02* (2006.01)
(Continued)

(52) U.S. Cl.
CPC ............ *A61M 1/1629* (2014.02); *A61M 1/16* (2013.01); *A61M 1/1698* (2013.01); *B01D 63/022* (2013.01); *A61M 2207/00* (2013.01); *B01D 2313/22* (2013.01); *B01D 2313/90* (2013.01); *B29C 53/8083* (2013.01); *B29L 2031/18* (2013.01); *B29L 2031/753* (2013.01); *F28D 21/0015* (2013.01); *F28D 2021/005* (2013.01)

(58) Field of Classification Search
CPC .... A61M 1/16; A61M 1/1629; A61M 1/1698; A61M 2207/00; B01D 63/022;
(Continued)

(56) References Cited

U.S. PATENT DOCUMENTS

| 4,572,446 A | 2/1986 | Leonard et al. |
| 9,867,919 B2 | 1/2018 | Eisuke et al. |

(Continued)

FOREIGN PATENT DOCUMENTS

| CN | 86105092 A | 5/1987 |
| CN | 86107524 A | 8/1987 |

(Continued)

OTHER PUBLICATIONS

Translation of PCT Written Opinion, PCT/JP2017/030332, dated Oct. 10, 2017.

(Continued)

*Primary Examiner* — Benjamin J Klein
(74) *Attorney, Agent, or Firm* — MacMillan, Sobanski & Todd, LLC

(57) ABSTRACT

A heat exchanger for an oxygenator device has multiple hollow fiber membranes that each have a hollow portion through which a heat medium passes, wherein the fibers are wound as a cylinder body. Each of the hollow fiber membranes follows a path between opposing ends of the cylinder body which is tilted with respect to a central axis of the cylinder body and is wound around the central axis of the cylinder body, wherein a tilt angle θ with respect to the central axis ranges from 22° to smaller than 67°, and wherein a constituent material of each of the hollow fiber membranes has a Young's modulus E ranging from 2.6 GPa to 0.07 GPa. During winding, the hollow fiber membranes are stretched according to a stretching rate between 0.5% and 3.0% and then fixed at the ends to maintain the stretching.

18 Claims, 12 Drawing Sheets

(51) Int. Cl.
*B29C 53/80* (2006.01)
*B29L 31/18* (2006.01)
*B29L 31/00* (2006.01)
*F28D 21/00* (2006.01)

(58) Field of Classification Search
CPC ...... B01D 63/025; B01D 69/08; B01D 71/48; B01D 71/56; B01D 2313/22; B01D 2313/90; B29C 53/8083; B29L 2031/18; B29L 2031/753; F28D 21/0015; F28D 2021/005
See application file for complete search history.

(56) References Cited

U.S. PATENT DOCUMENTS

| | | | |
|---|---|---|---|
| 2009/0098017 A1 | 4/2009 | Celik-Butler et al. | |
| 2010/0050875 A1 | 3/2010 | Ziembinski | |
| 2013/0071594 A1* | 3/2013 | Bikson | B64D 37/32 428/36.9 |
| 2017/0128621 A1* | 5/2017 | Sasaki | A61L 27/16 |

FOREIGN PATENT DOCUMENTS

| | | | | |
|---|---|---|---|---|
| CN | 104640619 A | | 5/2015 | |
| JP | S58169510 A | | 10/1983 | |
| JP | 2001162143 A | | 6/2001 | |
| JP | 3772909 B1 | * | 5/2006 | ......... B01D 67/0011 |
| WO | WO-2009119373 A1 | * | 10/2009 | ............ B01D 69/08 |
| WO | 2016009780 A1 | | 1/2016 | |

OTHER PUBLICATIONS

Japanese Office Action, 2018-537202, dated Apr. 20, 2021.
Extended European Search Report, EP Application 17846292.5, dated Feb. 24, 2020.
International Search Report, PCT/JP2017/030332, dated Oct. 10, 2017.
Chinese Office Action, 201780034116, dated Mar. 22, 2021.

* cited by examiner

HEAT EXCHANGER, OXYGENATOR, AND METHOD OF MANUFACTURING A HEAT EXCHANGER

CROSS REFERENCE TO RELATED APPLICATIONS

This application is a continuation of PCT Application No. PCT/JP2017/030332, filed Aug. 24, 2017, based on and claiming priority to Japanese Application No. 2016-169931, filed Aug. 31, 2016, both of which are incorporated herein by reference in their entirety.

BACKGROUND OF THE INVENTION

The present invention relates to a heat exchanger, an oxygenator, and a method of manufacturing a heat exchanger.

In the related art, there is a known oxygenator having a configuration in which heat exchange is performed by using a hollow fiber membrane layer configured with multiple hollow fiber membranes (for example, refer to U.S. Patent Application Publication 2016/0331882A1). In the oxygenator disclosed in US2016/0331882A1, the hollow fiber membrane layer is formed in a shape of a cylinder body by laminating multiple hollow fiber membranes. In each layer, each one of the hollow fiber membranes is wound around a central axis of the cylinder body and is disposed from one end side toward the other end side of the cylinder body. Each of the hollow fiber membranes wound in this manner has a problem that a pressure loss of a heat medium passing through the inside of the hollow fiber membrane increases in proportion to the increase in the length per one hollow fiber thereof.

Moreover, in order to solve the problem described above, it is assumed to use hollow fiber membranes having a comparatively large inner diameter. However, if the inner diameter of the hollow fiber membrane is increased, the outer diameter is also increased. As a result, the total useful area lost as a result of a gap between the hollow fiber membranes increases. Accordingly, there is also a problem that the amount of blood passing through the gap, that is, a blood filling amount increases, so that a burden on a patient becomes significant.

SUMMARY OF THE INVENTION

An object of the present invention is to provide a heat exchanger, in which a pressure loss of a heat medium passing through each of hollow fiber membranes can be prevented as much as possible and reduction of a filling amount of liquid (for example, blood) which is a target of heat exchange inside the heat exchanger can be achieved.

The object is realized through a heat exchanger including multiple hollow fiber membranes that each have a hollow portion through which a heat medium passes, and exhibiting a shape of a cylinder body as a whole shape in which the multiple hollow fiber membranes are integrated. Each of the hollow fiber membranes is tilted with respect to a central axis of the cylinder body and is wound around the central axis of the cylinder body. A tilt angle θ with respect to the central axis of the cylinder body of each of the hollow fiber membranes preferably ranges from 22° to smaller than 67°. A constituent material of each of the hollow fiber membranes preferably has a Young's modulus E of 2.6 GPa or smaller. Preferably, the Young's modulus E is also 0.07 GPa or greater.

In the heat exchanger, the constituent material of each of the hollow fiber membranes is preferably a polyamide-based resin material or a polyester-based resin material.

In the heat exchanger, the hollow fiber membrane preferably has an outer diameter of 1 mm or smaller.

The invention discloses a method of manufacturing a heat exchanger including multiple hollow fiber membranes that each have a hollow portion through which a heat medium passes, and exhibiting a shape of a cylinder body as a whole shape in which the multiple hollow fiber membranes are integrated. The method includes a winding step of winding each of the hollow fiber membranes around a central axis of the cylinder body while the hollow fiber membrane is tilted with respect to the central axis of the cylinder body in a pulled state where the hollow fiber membrane is pulled in a longitudinal direction of the hollow fiber membrane. In the winding step, a stretching rate of each of the hollow fiber membranes in the pulled state ranges from 0.5% to 3%, and a tilt angle θ with respect to the central axis of the cylinder body of each of the hollow fiber membranes ranges from 22° to smaller than 67°. A constituent material of each of the hollow fiber membranes preferably has a Young's modulus E of 2.6 GPa or smaller.

In the method of manufacturing a heat exchanger, the Young's modulus E is preferably 0.07 GPa or greater.

In the method of manufacturing a heat exchanger, the constituent material of each of the hollow fiber membranes is preferably a polyamide-based resin material or a polyester-based resin material.

In the method of manufacturing a heat exchanger, the hollow fiber membrane preferably has an outer diameter of 1 mm or smaller.

In the method of manufacturing a heat exchanger, the heat exchanger preferably exhibits a cylindrical shape and has a core around which each of the hollow fiber membranes is wound. In the winding step, each of the hollow fiber membranes is wound by reciprocating each of the hollow fiber membranes on an outer peripheral portion of the core in a central axis direction of the cylinder body. In the winding step, when each of the hollow fiber membranes is reciprocating, a turned-back portion is formed by causing the hollow fiber membrane to be turned back on both one side and the other side of the cylinder body, and the turned-back portion is fixed by winding a fixing string around the central axis of the cylinder body in the vicinity of the turned-back portion in an overlapping manner.

In the method of manufacturing a heat exchanger, a stepped portion having the core reduced in outer diameter is formed at both end portions of the outer peripheral portion of the core. When the fixing string is viewed from the outer peripheral portion side of the core, the fixing string is disposed in a manner overlapping the stepped portions at both the end portions.

In the method of manufacturing a heat exchanger, a groove is preferably formed along a circumferential direction of the outer peripheral portion which is recessed at both the end portions of the outer peripheral portion of the core. When the fixing string is viewed from the outer peripheral portion side of the core, the fixing string is disposed in a manner overlapping the grooves at both the end portions.

According to the present invention, the entire length of the hollow fiber membrane can be shortened to an extent that a heat exchange function per one hollow fiber membrane is not impaired. Accordingly, a pressure loss of the heat medium passing through the hollow fiber membrane can be prevented as much as possible. Thus, liquid which is a target of heat exchange can be smoothly and promptly subjected to heat exchange.

In addition, the hollow fiber membrane can be reduced in diameter as much as possible, by the reduced amount of the pressure loss of the heat medium described above. Accordingly, the total capacity lost due to a gap between the hollow fiber membranes can be reduced, and a filling amount of a fluid which is a target of heat exchange can be reduced.

Since each of the hollow fiber membranes is configured with a material having the Young's modulus E of 2.6 GPa or smaller, and the hollow fiber membrane is in the pulled state where the stretching rate ranges from 0.5% to 3% during a process of manufacturing a heat exchanger, although the hollow fiber membrane is stretched and is reduced in diameter, the degree of diameter reduction can be prevented from being excessive, that is, the hollow fiber membrane can be prevented from being squashed. Accordingly, a heat medium can smoothly pass through the inside of the hollow fiber membrane, which leads to prevention of a pressure loss. In addition, the gap between the hollow fibers can be prevented from excessively increasing by controlling the extent of diameter reduction of the hollow fiber membrane, that is, by controlling the degree of diameter reduction of the hollow fiber membrane. Accordingly, a blood filling amount can be restrained from increasing.

DETAILED DESCRIPTION OF PREFERRED EMBODIMENTS

Hereinafter, a heat exchanger, an oxygenator, and a method of manufacturing a heat exchanger of the present invention will be described based on preferable embodiments illustrated in the accompanying drawings.

First Embodiment

Figure 1:
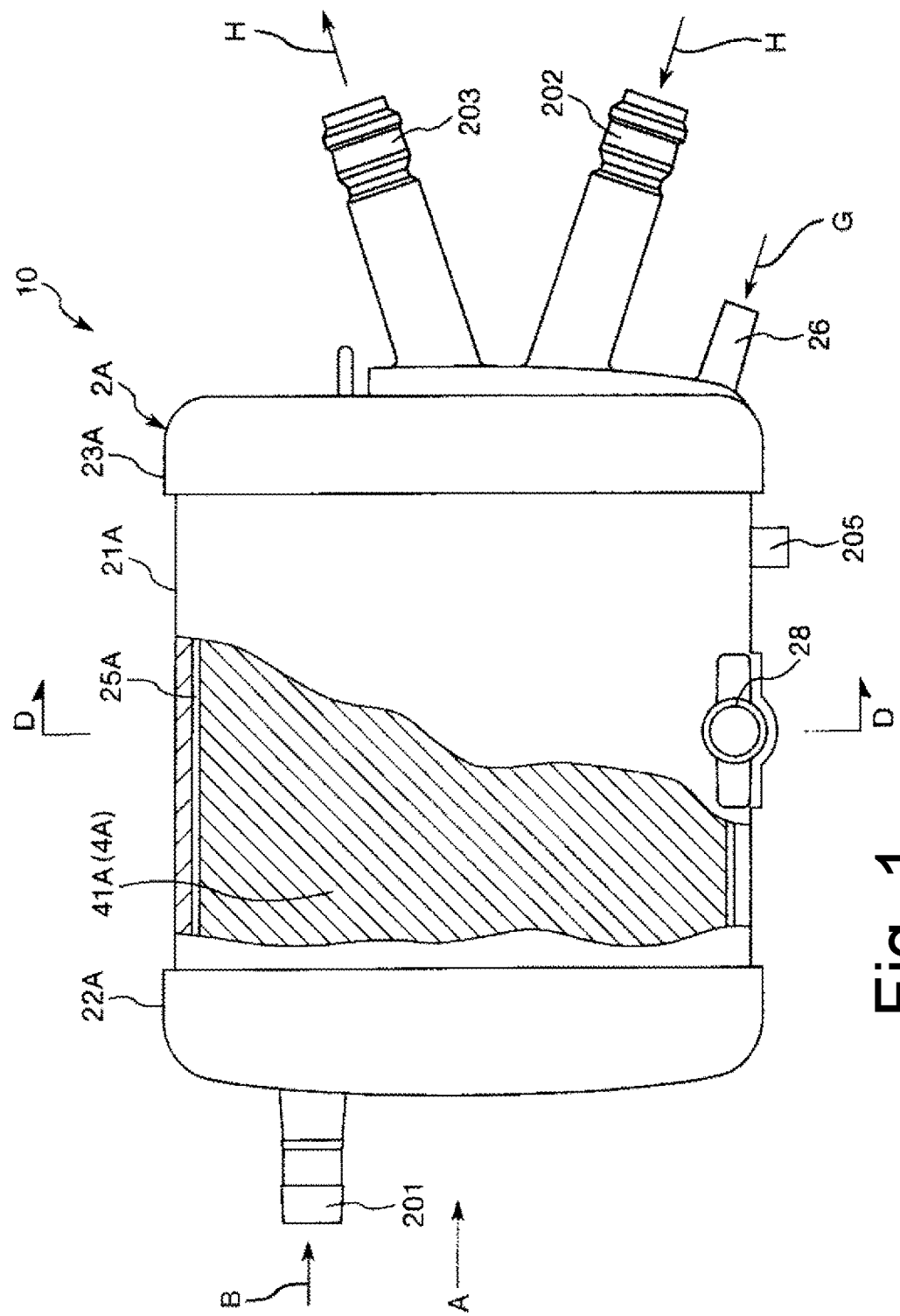
FIG. 1 is a plan view of an oxygenator internally including a heat exchanger of the present invention.
Figure 2:
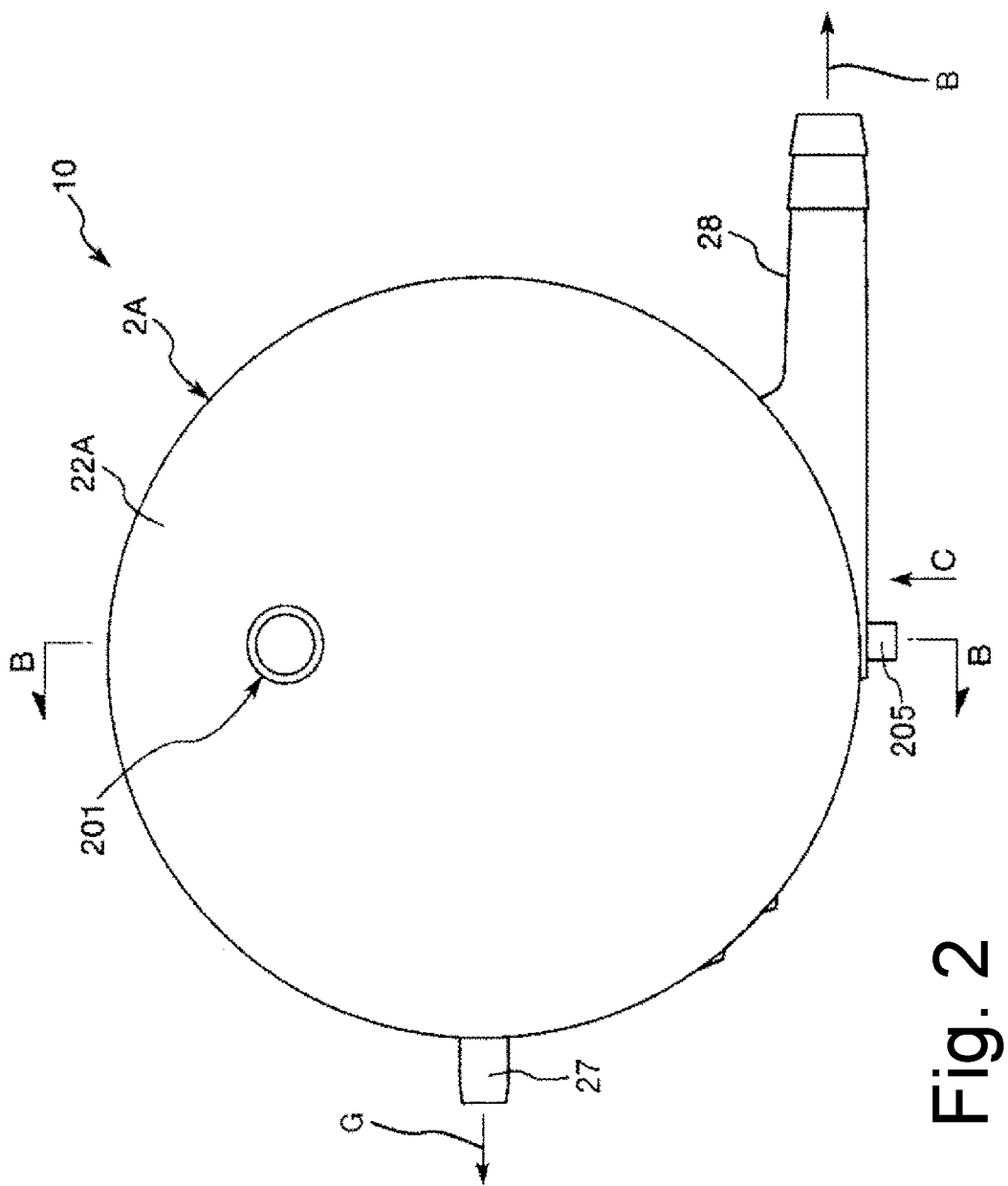
FIG. 2 is a view when the oxygenator illustrated in FIG. 1 is viewed in an arrow A direction.
Figure 3:
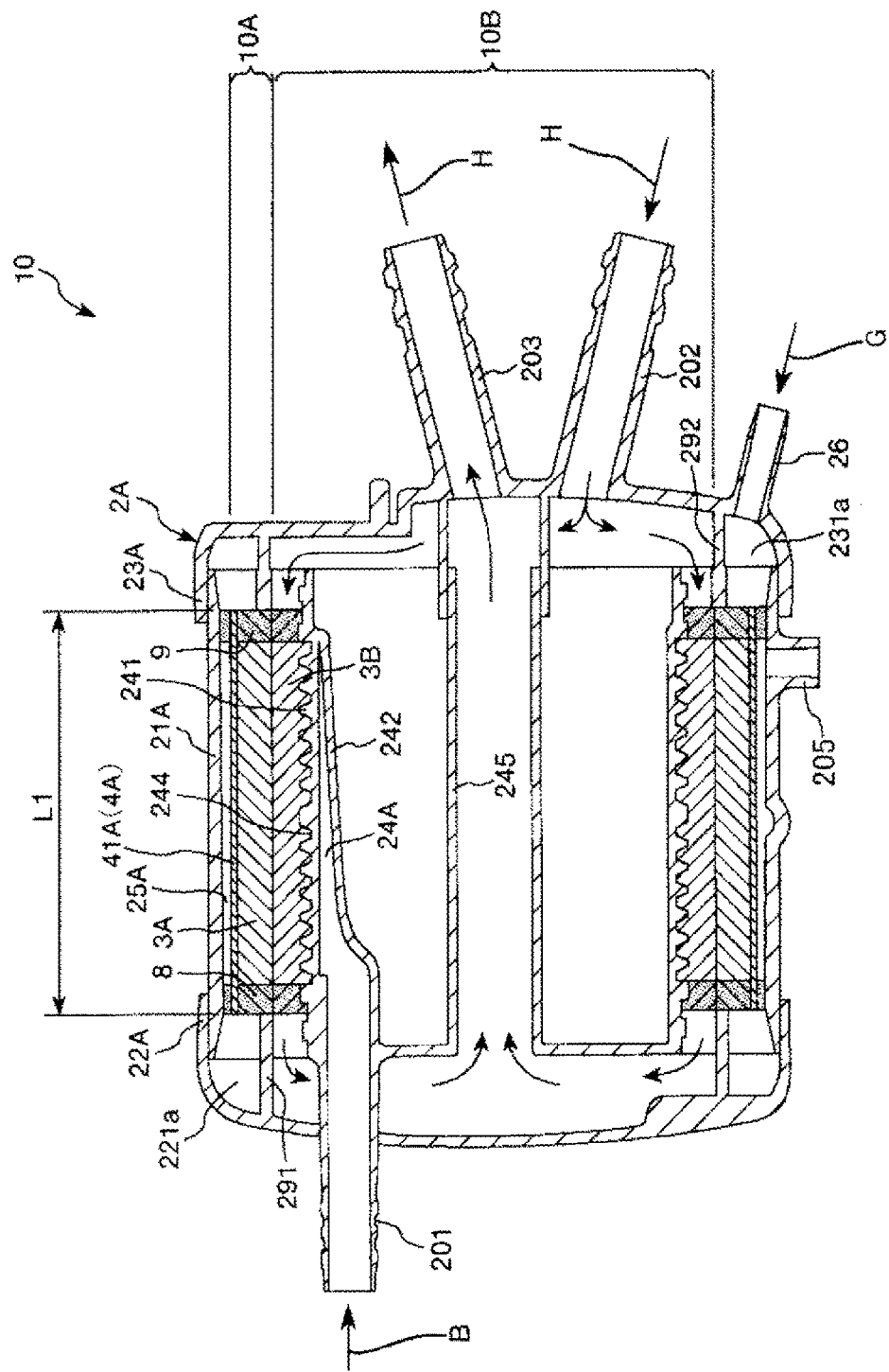
FIG. 3 is a cross-sectional view taken along line B-B in FIG. 2.
Figure 4:
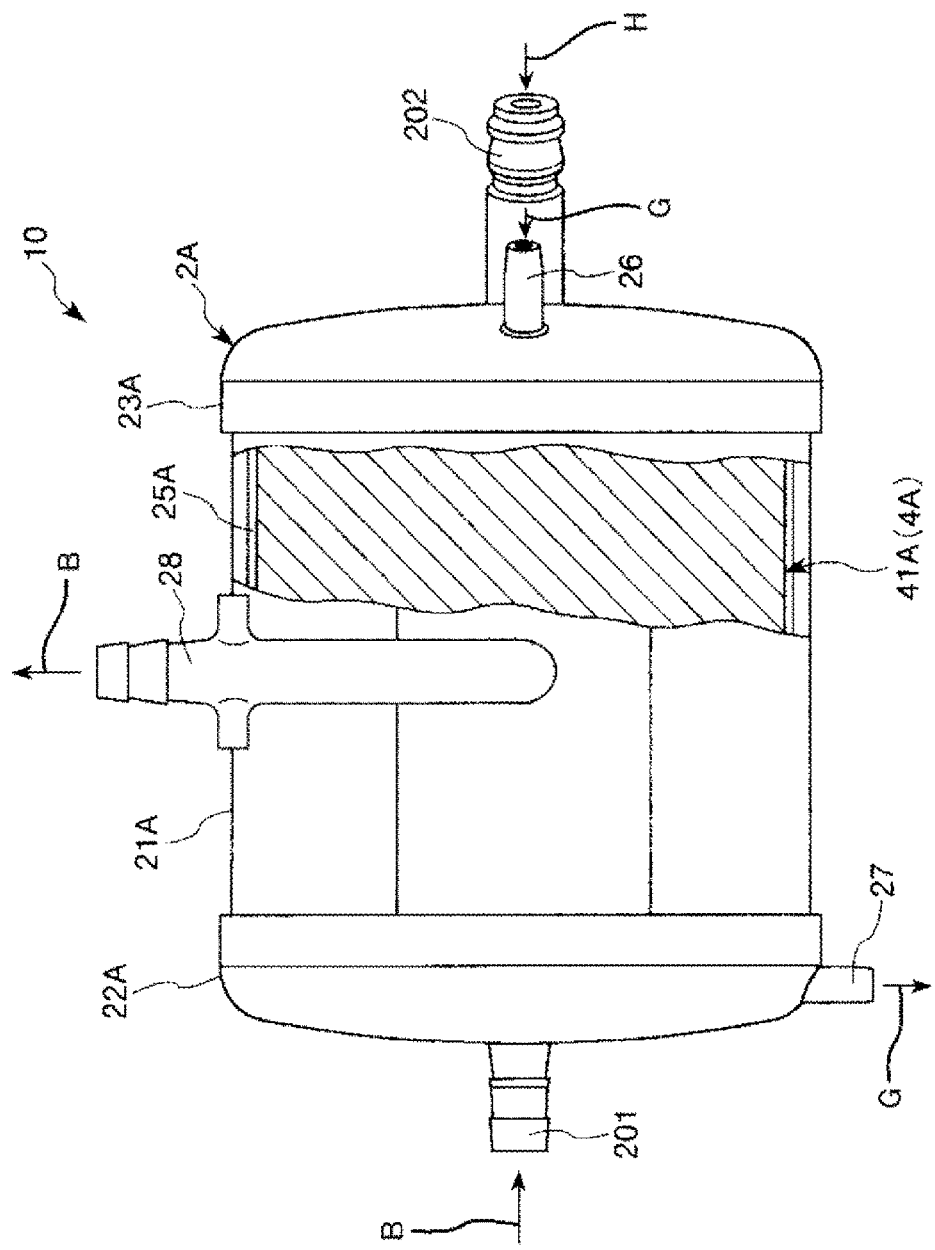
FIG. 4 is a view when viewed in an arrow C direction in FIG. 2.
Figure 5:
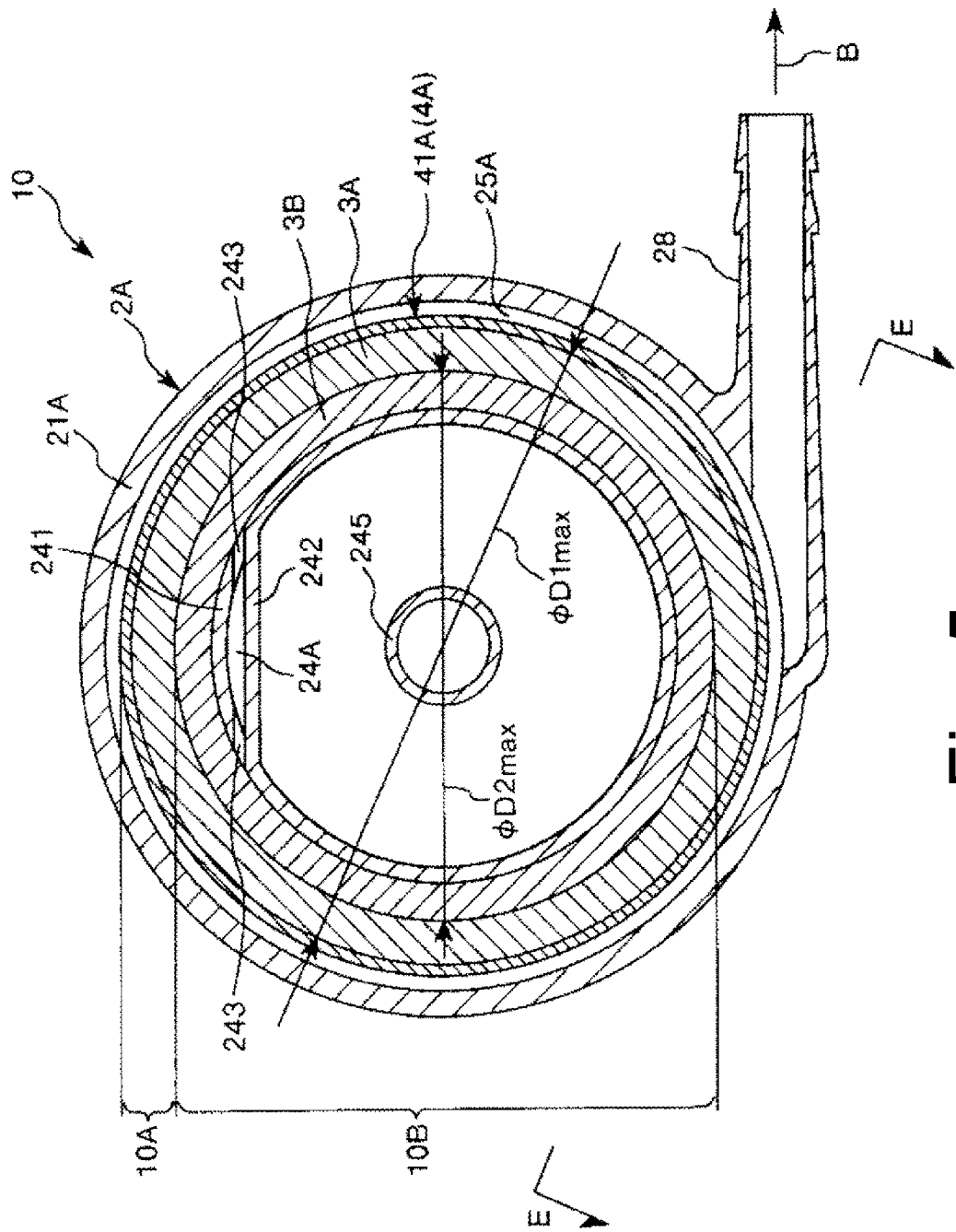
FIG. 5 is a cross-sectional view taken along line D-D in FIG. 1.
Figure 6:
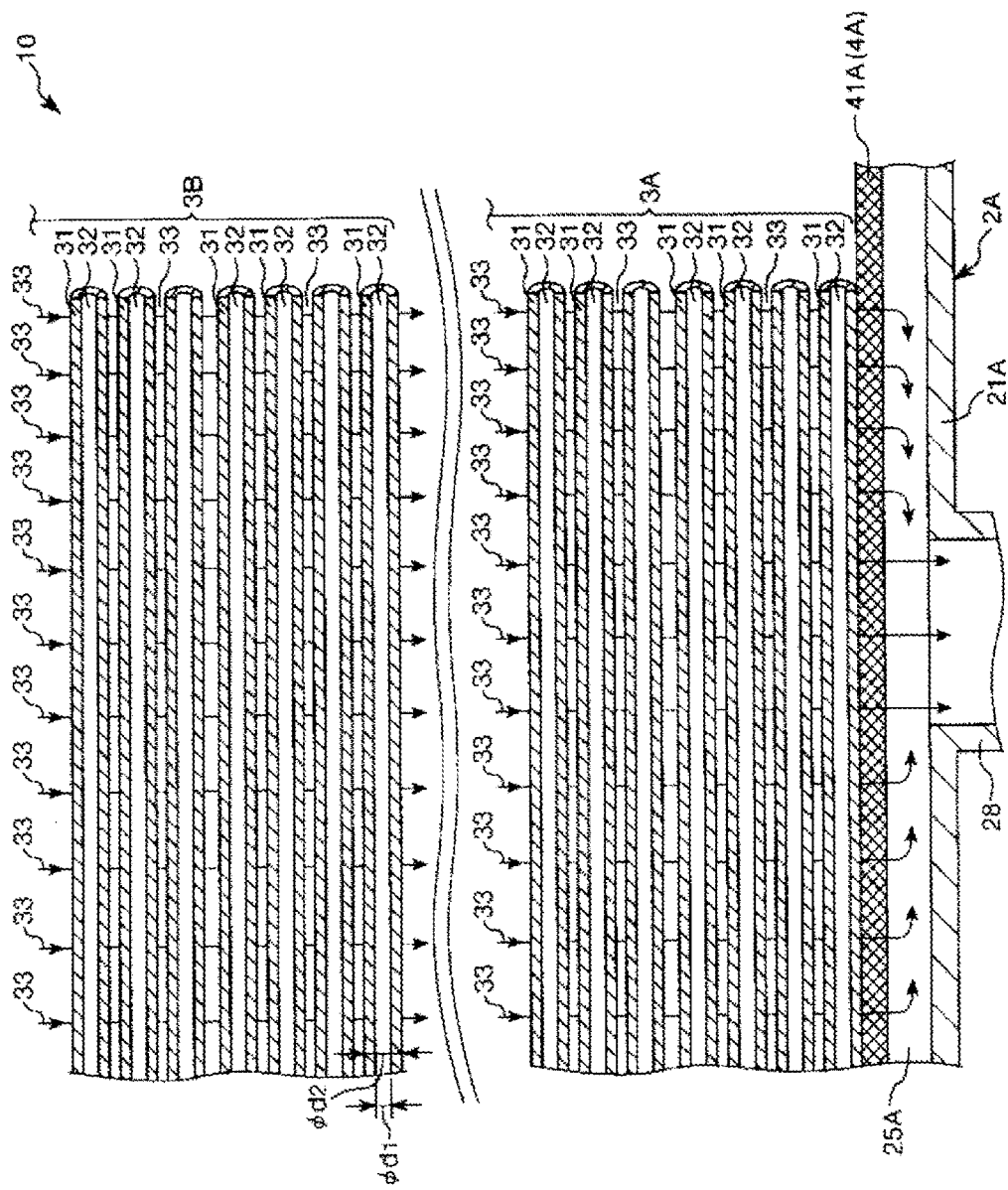
FIG. 6 is a cross-sectional view taken along line E-E in FIG. 5.
Figure 7:
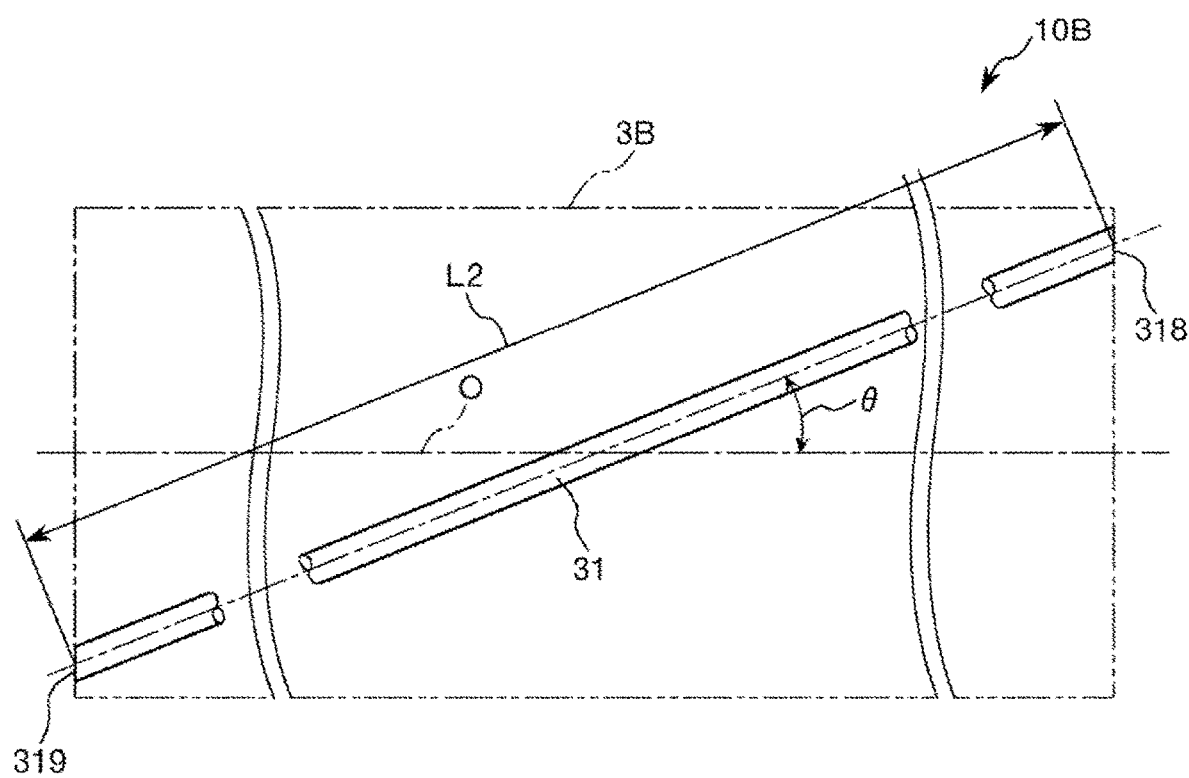
FIG. 7 is a schematic side view of the heat exchanger of the present invention.
Figure 8:
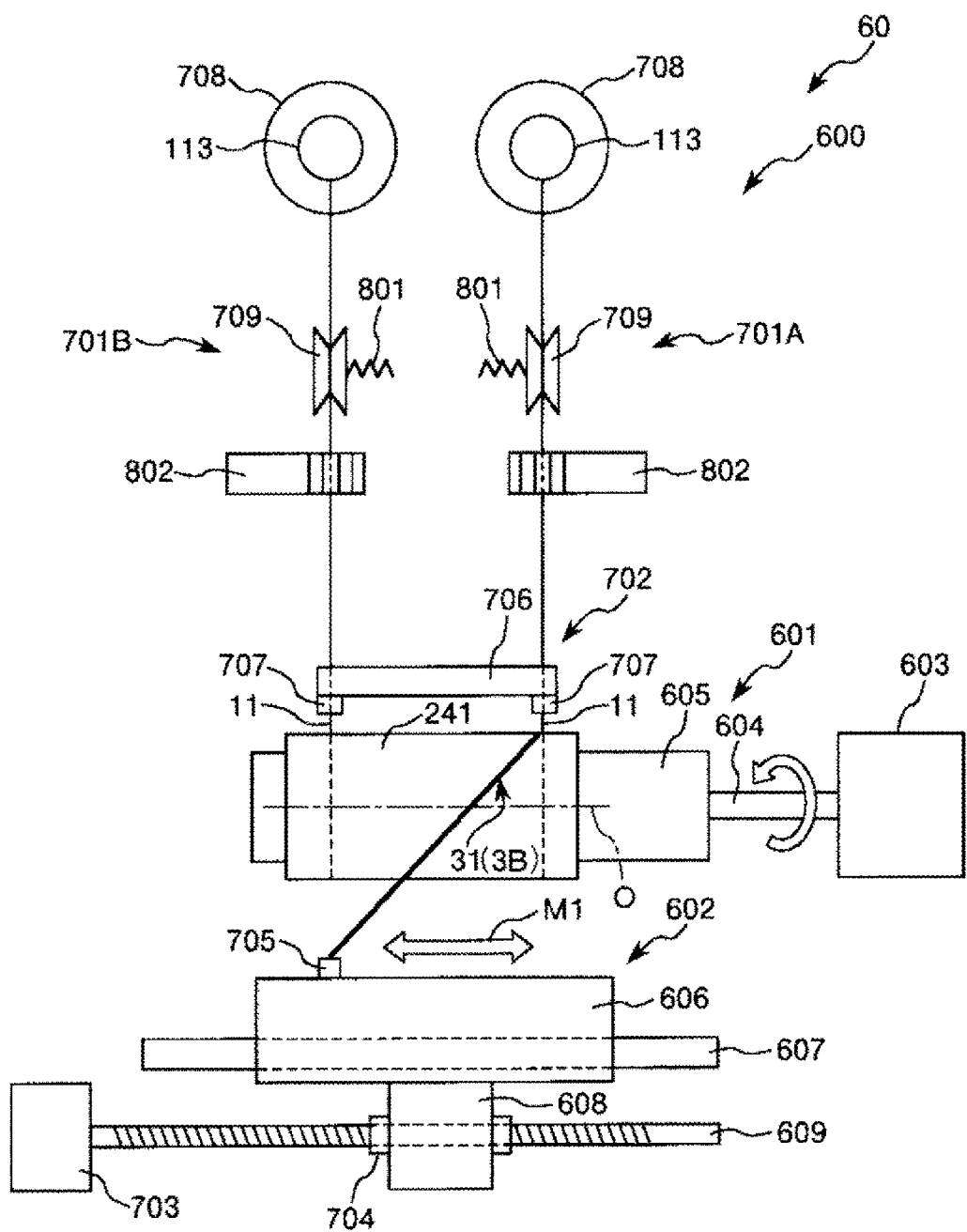
FIG. 8 is a view illustrating a device used in a method of manufacturing the heat exchanger of the present invention.
Figure 9:
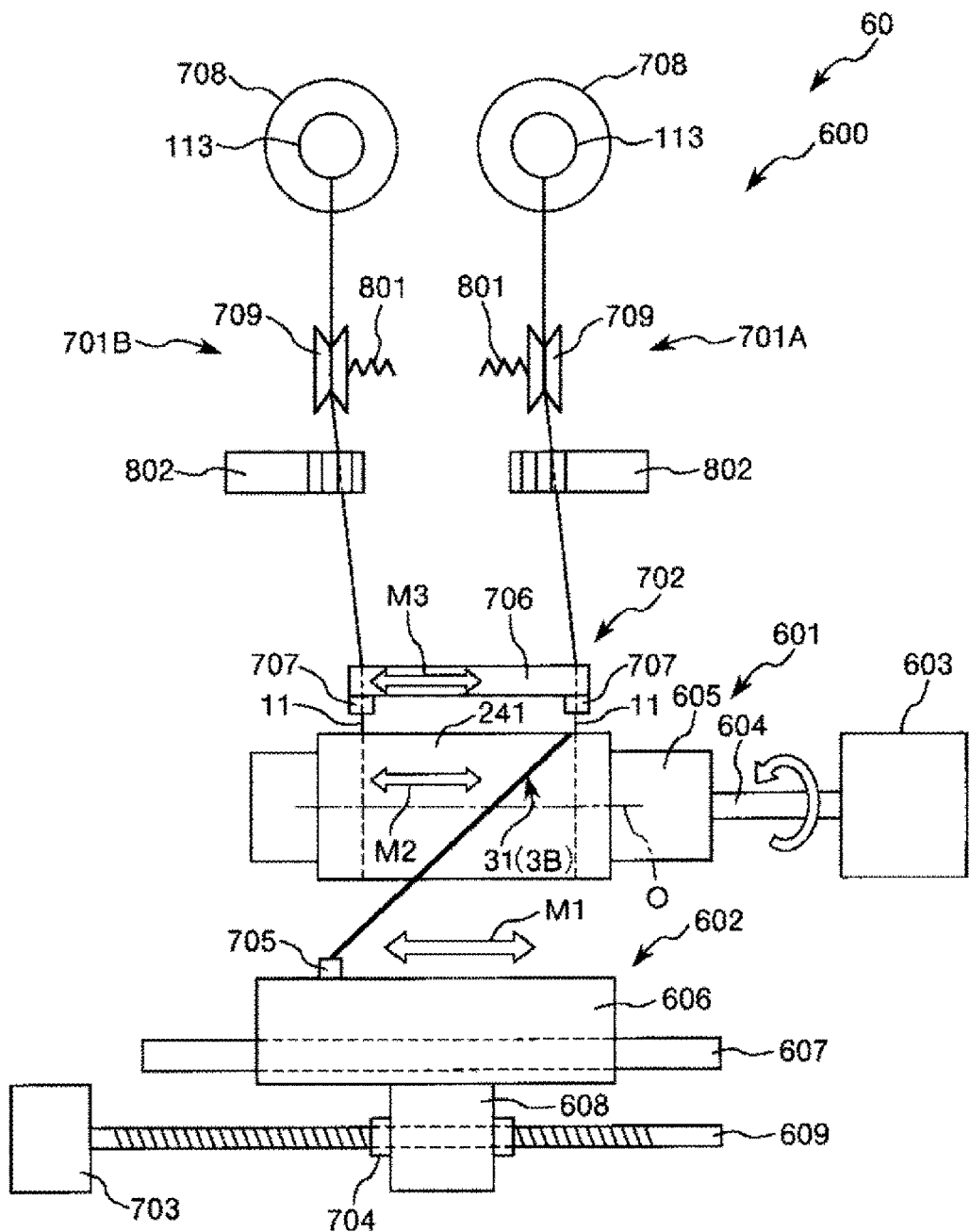
FIG. 9 is another view illustrating the device used in the method of manufacturing the heat exchanger of the present invention.
Figure 10:
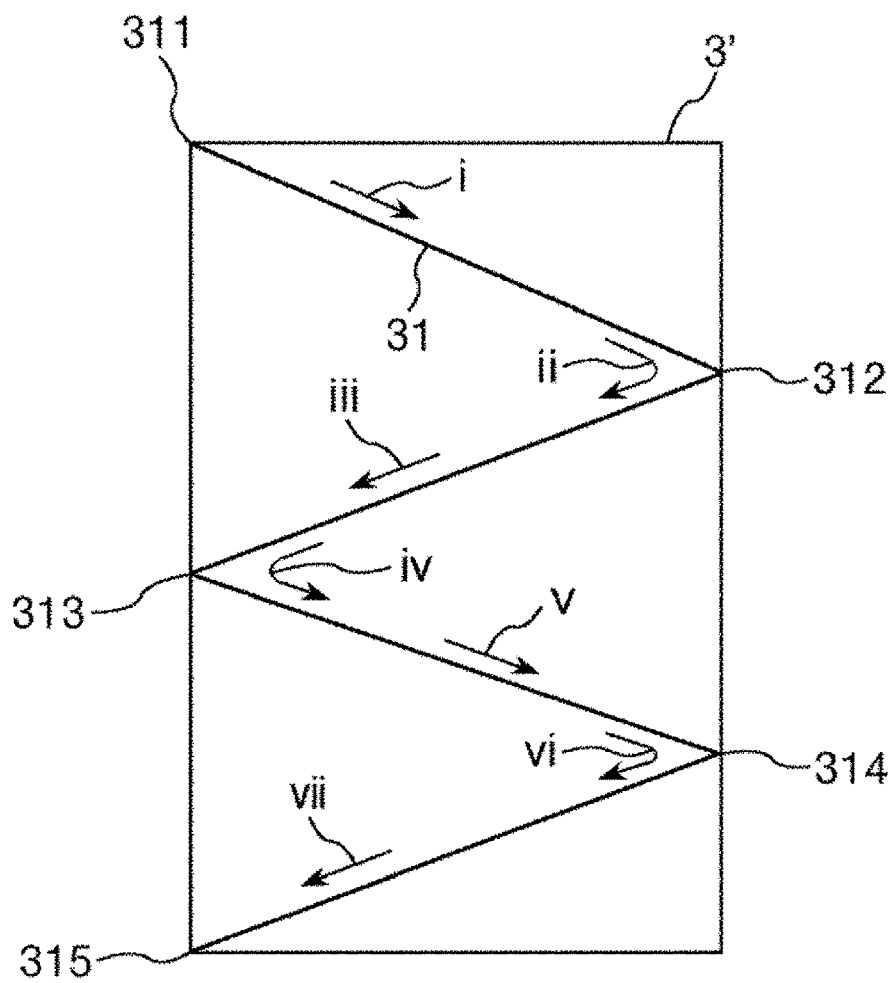
FIG. 10 is an example of a development view of a base material of the heat exchanger manufactured by the device illustrated in FIGS. 8 and 9.
Figure 11:
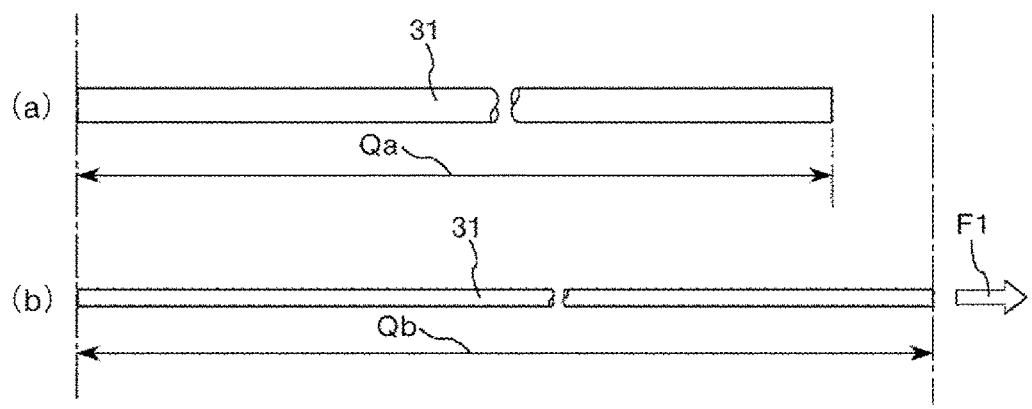
FIG. 11 is a view for describing a pulled state of a hollow fiber membrane during a process of manufacturing a heat exchanger.
Figure 12A:
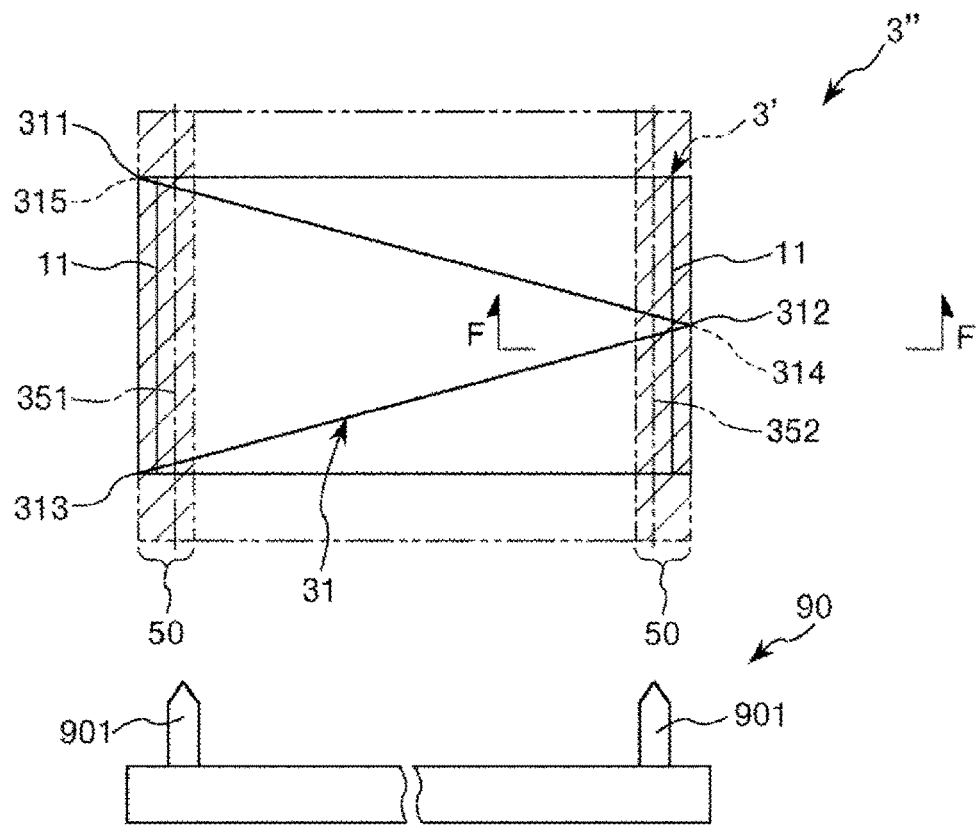
FIGS. 12A and 12B are views sequentially illustrating a step of cutting the base material illustrated in FIG. 10.
Figure 12B:
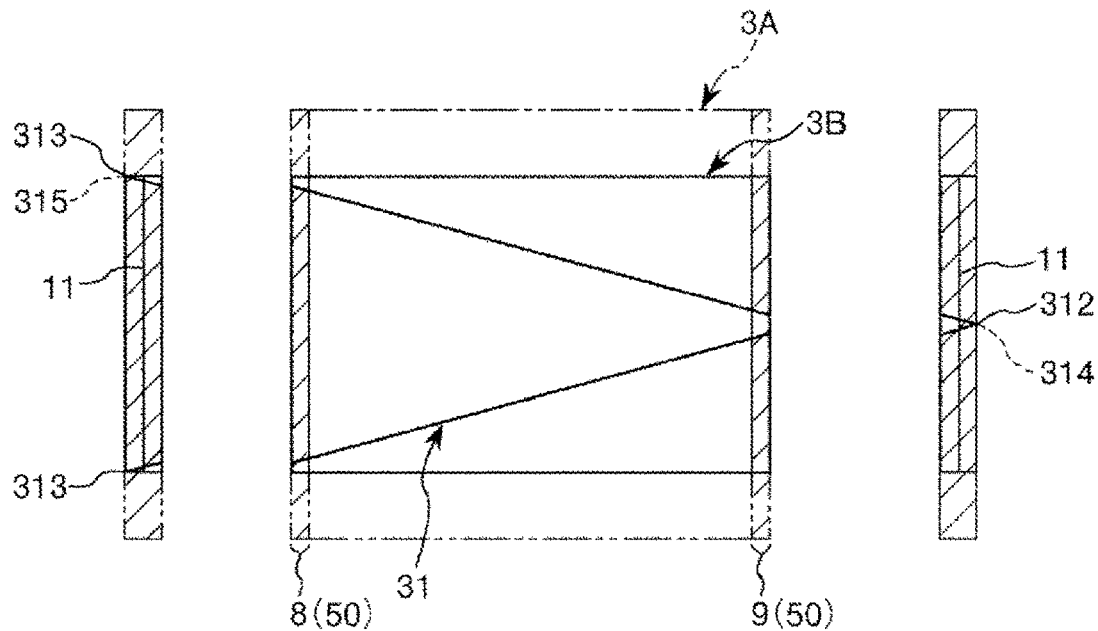
Figure 13:
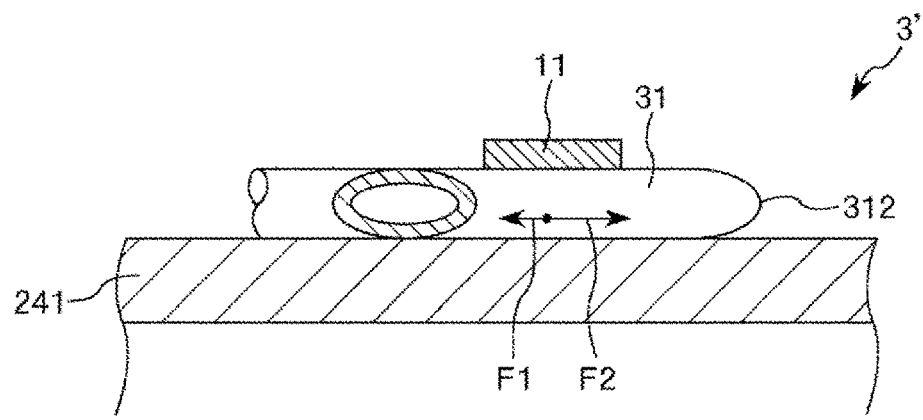
FIG. 13 is a cross-sectional view taken along line F-F in FIG. 12A.

FIG. 1 is a plan view of an oxygenator internally including a heat exchanger of the present invention. FIG. 2 is a view when the oxygenator illustrated in FIG. 1 is viewed in an arrow A direction. FIG. 3 is a cross-sectional view taken along line B-B in FIG. 2. FIG. 4 is a view when viewed in an arrow C direction in FIG. 2. FIG. 5 is a cross-sectional view taken along line D-D in FIG. 1. FIG. 6 is a cross-sectional view taken along line E-E in FIG. 5. FIG. 7 is a schematic side view of the heat exchanger of the present invention. FIGS. 8 and 9 are views illustrating a device used in a method of manufacturing the heat exchanger of the present invention, respectively. FIG. 10 is an example of a development view of a base material of the heat exchanger manufactured by the device illustrated in FIGS. 8 and 9. FIG. 11 is a view for describing a pulled state of a hollow fiber membrane during a process of manufacturing a heat exchanger. FIGS. 12A and 12B are views sequentially illustrating a step of cutting the base material illustrated in FIG. 10. FIG. 13 is a cross-sectional view taken along line F-F in FIG. 12. Note that, the left sides in FIGS. 1, 3, 4, 7 to 9, 12, and 13 (the same applies to FIGS. 14 and 15) will be referred to as "left" or "leftward (one side)" and the right sides therein will be referred to as "right" or "rightward (the other side)". In addition, in FIGS. 1 to 6, the inside of the oxygenator will be described as "blood inflow side" or "upstream side" and the outside thereof will be described as "blood outflow side" or "downstream side". In addition, in FIGS. 7, 10, and 12, one hollow fiber membrane is representatively depicted in an exaggerated manner.

An oxygenator 10 illustrated in FIGS. 1 to 5 is an oxygenator equipped with a heat exchanger, which internally includes the heat exchanger performing heat exchange with respect to blood B. This oxygenator 10 has a substantially columnar shape in its entirety and includes a heat exchange section 10B which is provided inside thereof and serves as a heat exchanger, and an oxygenator section 10A which is provided on the outer circumferential side of the heat exchange section 10B and serves as a gas exchanger exchanging gas with respect to the blood B. For example, the oxygenator 10 is used by being installed in an extracorporeal blood circulation loop. Accordingly, the blood B is subjected to heat exchange and gas exchange by the oxygenator 10 during a process of passing through the extracorporeal blood circulation loop and returns to the inside of the body of a patient.

The oxygenator 10 has a housing 2A, and the oxygenator section 10A and the heat exchange section 10B are accommodated inside the housing 2A.

The housing 2A is configured to have a cylindrical housing main body 21A, a disk-shaped first lid 22A which seals a left end opening of the cylindrical housing main body 21A, and a disk-shaped second lid 23A which seals a right end opening of the cylindrical housing main body 21A.

The cylindrical housing main body 21A, the first lid 22A, and the second lid 23A are formed of resin materials. The first lid 22A and the second lid 23A are fixedly attached to the cylindrical housing main body 21A through a method such as welding and bonding which is performed by using an adhesive.

A pipe-shaped blood outflow port 28 is formed in an outer peripheral portion of the cylindrical housing main body 21A. The blood outflow port 28 protrudes substantially in a tangential direction of an outer peripheral surface of the cylindrical housing main body 21A (refer to FIG. 5).

A pipe-shaped purge port 205 is protrusively formed in the outer peripheral portion of the cylindrical housing main body 21A. The purge port 205 is formed in the outer peripheral portion of the cylindrical housing main body 21A such that a central axis thereof intersects a central axis of the cylindrical housing main body 21A.

A pipe-shaped gas outflow port 27 is protrusively formed in the first lid 22A. The gas outflow port 27 is formed in the outer peripheral portion of the first lid 22A such that the central axis intersects the center of the first lid 22A (refer to FIG. 2).

In addition, a blood inflow port 201 protrudes from an end surface of the first lid 22A such that a central axis thereof becomes eccentric with respect to the center of the first lid 22A.

A pipe-shaped gas inflow port 26, a heat medium inflow port 202, and a heat medium outflow port 203 are protrusively formed in the second lid 23A. The gas inflow port 26 is formed at an edge portion on the end surface of the second lid 23A. Each of the heat medium inflow port 202 and the heat medium outflow port 203 is formed substantially in a central portion on the end surface of the second lid 23A. In addition, the center lines of the heat medium inflow port 202 and the heat medium outflow port 203 are respectively and slightly tilted with respect to the center line of the second lid 23A.

Note that, in the present invention, the whole shape of the housing 2A is not necessarily a completely columnar shape. For example, the housing 2A may have a shape partially lacking, a shape to which a variant portion is added, or the like.

As illustrated in FIGS. 3 and 5, the cylindrical oxygenator section 10A is accommodated inside the housing 2A along the inner peripheral surface. The oxygenator section 10A is configured to have a cylindrical hollow fiber membrane bundle 3A and a filter member 41A which serves as air bubble removal means 4A provided on the outer peripheral side of the hollow fiber membrane bundle 3A. The hollow fiber membrane bundle 3A and the filter member 41A are disposed in the order of the hollow fiber membrane bundle 3A and the filter member 41A from the blood inflow side.

In addition, the heat exchange section 10B is installed inside the oxygenator section 10A. As a whole shape, the heat exchange section 10B exhibits a cylindrical shape (shape of a cylinder body) along an inner peripheral surface of the oxygenator section 10A, and has a hollow fiber membrane bundle 3B.

As illustrated in FIG. 6, each of the hollow fiber membrane bundle 3A and the hollow fiber membrane bundle 3B is configured with multiple hollow fiber membranes 31 and is formed by integrating and laminating the hollow fiber membranes 31 in a layered manner. The number of laminated layers is not particularly limited. For example, it is preferable to have 3 to 40 layers. Note that, each of the hollow fiber membranes 31 constituting the hollow fiber membrane bundle 3A has a function of exchanging gas with a blood flow making contact with an outer surface of membranes 31 in bundle 3A. Meanwhile, each of the hollow fiber membranes 31 constituting the hollow fiber membrane bundle 3B has a function of exchanging heat with a blood flow making contact with an outer surface of membranes 31 in bundle 3B.

As illustrated in FIG. 3, both end portions of each of the hollow fiber membrane bundle 3A and the hollow fiber membrane bundle 3B are collectively fixed to the inner surface of the cylindrical housing main body 21A through a partition wall 8 and a partition wall 9. For example, the partition wall 8 and the partition wall 9 are configured with a potting material such as polyurethane and silicone rubber, an adhesive, or the like. Moreover, an inner peripheral portion of the hollow fiber membrane bundle 3B engages with an uneven (i.e., non-flat) portion 244 formed in the outer peripheral portion of a first cylinder member 241. Due to the engagement and the state of being fixed through the partition wall 8 and the partition wall 9, the hollow fiber membrane bundle 3B is reliably fixed to the cylindrical housing main body 21A. Thus, it is possible to reliably prevent positional deviation of the hollow fiber membrane bundle 3B while the oxygenator 10 is in use. In addition, the uneven portion 244 also functions as a flow path for allowing the blood B to circumambulate the hollow fiber membrane bundle 3B in its entirety.

Note that, as illustrated in FIG. 5, for example, a maximum outer diameter $\phi D1_{max}$ of the hollow fiber membrane bundle 3A preferably ranges from 20 mm to 200 mm and more preferably ranges from 40 mm to 150 mm. For example, a maximum outer diameter $\phi D2_{max}$ of the hollow fiber membrane bundle 3B preferably ranges from 10 mm to 150 mm and more preferably ranges from 20 mm to 100 mm. In addition, as illustrated in FIG. 3, longitudinal lengths L1 of the hollow fiber membrane bundle 3A and the hollow fiber membrane bundle 3B along a central axis direction are the same as each other. For example, the length L1 preferably ranges from 30 mm to 250 mm and more preferably ranges from 50 mm to 200 mm. When such conditions are met, the hollow fiber membrane bundle 3A has an excellent function of exchanging gas, and the hollow fiber membrane bundle 3B has an excellent function of exchanging heat.

In addition, between the partition wall 8 and the partition wall 9 inside the housing 2A, a gap formed between the hollow fiber membranes 31 functions as a blood flow path 33 through which the blood B flows from the upper side toward the lower side in FIG. 6.

A blood inflow side space 24A which serves as a blood inflow portion of the blood B flowed in through the blood inflow port 201 and communicates with the blood inflow port 201 is formed on the upstream side of the blood flow path 33 (refer to FIGS. 3 and 5).

The blood inflow side space 24A is a space defined by the first cylinder member 241 exhibiting a cylindrical shape and a plate piece 242 that is disposed inside the first cylinder member 241 and is disposed so as to face a part of the inner peripheral portion thereof. The blood B which has flowed into the blood inflow side space 24A can be distributed through the blood flow path 33 in its entirety via a plurality of side holes 243 formed in the first cylinder member 241.

In addition, the first cylinder member 241 constitutes a part of the heat exchanger and is also used as a core around which each of the hollow fiber membranes 31 is wound during a process of manufacturing thereof as described below.

A second cylinder member 245 disposed concentrically with the first cylinder member 241 is disposed inside the first cylinder member 241. As illustrated in FIG. 3, a heat medium H (for example, water or hot water) which has flowed in through the heat medium inflow port 202 passes through the inside of each of the hollow fiber membranes 31 of the hollow fiber membrane bundle 3B on the outer circumferential side of the first cylinder member 241 and the inner side of the second cylinder member 245 in order, thereby being discharged through the heat medium outflow port 203. In addition, when the heat medium H passes through a flow path 32 constituted of a hollow portion of each of the hollow fiber membranes 31, heat exchange (heating or cooling) is performed between the heat medium H and the blood B coming into contact with the hollow fiber membranes 31 inside the blood flow path 33 (refer to FIG. 6).

The filter member 41A which has a function of capturing air bubbles present in the blood B flowing in the blood flow path 33 is disposed on the downstream side of the blood flow path 33.

The filter member 41A is configured with a substantially rectangular sheet-like member (hereinafter, will be simply referred to as "sheet" as well) and is formed by winding the sheet along the outer periphery of the hollow fiber membrane bundle 3A. Both end portions of the filter member 41A are also fixedly attached to the partition wall 8 and the partition wall 9, respectively. Accordingly, the filter member 41A is fixed to the housing 2A (refer to FIG. 3). Note that, it is preferable that this filter member 41A is provided such that the inner peripheral surface comes into contact with the outer peripheral surface of the hollow fiber membrane bundle 3A and covers substantially the whole surface of the outer peripheral surface. Air bubbles captured by the filter member 41A are thrust due to a blood flow and enter the inside of each of the hollow fiber membranes 31 in the vicinity of the filter member 41A. As a result, the air bubbles are removed from the blood flow path 33.

In addition, a cylindrical gap is formed between the outer peripheral surface of the filter member 41A and the inner peripheral surface of the cylindrical housing main body 21A, and the gap forms a blood outflow side space 25A. The blood outflow side space 25A and the blood outflow port 28 communicating with the blood outflow side space 25A form a blood outflow portion. Since the blood outflow portion has the blood outflow side space 25A, a space for the blood B which has penetrated the filter member 41A and flows toward the blood outflow port 28 is ensured, and thus, the blood B can be smoothly discharged.

As illustrated in FIG. 3, a toric rib 291 is protrusively formed inside the first lid 22A. The first lid 22A, the rib 291, and the partition wall 8 define a first room 221a. The first room 221a is a gas outflow chamber from which the gas G flows out. The left end opening of each of the hollow fiber membranes 31 of the hollow fiber membrane bundle 3A is open to the first room 221a and communicates therewith. In the oxygenator 10, a gas outflow portion is configured with the gas outflow port 27 and the first room 221a. Meanwhile, a toric rib 292 is protrusively formed inside the second lid 23A as well. The second lid 23A, the rib 292, and the partition wall 9 define a second room 231a. The second room 231a is a gas inflow chamber to which the gas G flows in. The right end opening of each of the hollow fiber membranes 31 of the hollow fiber membrane bundle 3A is open to the second room 231a and communicates therewith. In the oxygenator 10, a gas inflow portion is configured with the gas inflow port 26 and the second room 231a.

Now, a flow of blood B in the oxygenator 10 of the present embodiment will be described. In the oxygenator 10, the blood B which has flowed in through the blood inflow port 201 passes through the blood inflow side space 24A and the side hole 243 in order, thereby flowing into the heat exchange section 10B. In the heat exchange section 10B, while flowing in the blood flow path 33 in a downstream direction, the blood B comes into contact with an outer surface of each of the hollow fiber membranes 31 of the heat exchange section 10B such that heat exchange (heating or cooling) is performed. The blood B subjected to heat exchange as described above flows into the oxygenator section 10A.

In the oxygenator section 10A, the blood B flows further in the blood flow path 33 in the downstream direction. Meanwhile, gas G (gas including oxygen) supplied through the gas inflow port 26 is distributed from the second room 231a to the flow paths 32 of each of the hollow fiber membranes 31 of the oxygenator section 10A and flows in the flow paths 32. Thereafter, the gas is integrated in the first room 221a and is discharged through the gas outflow port 27. The blood B flowing in the blood flow path 33 comes into contact with the outer surface of each of the hollow fiber membranes 31 of the oxygenator section 10A. Then, gas exchange, that is, oxygenation and decarbonation is performed between the flow paths 32 and the gas G flowing therein.

In a case where the blood B after gas exchange is intermixed with air bubbles, the air bubbles are captured by the filter member 41A, thereby being prevented from flowing out to the downstream side of the filter member 41A.

After the blood B is subjected to heat exchange and gas exchange in order and air bubbles are additionally removed, the blood B flows out through the blood outflow port 28.

As described above, both the hollow fiber membrane bundle 3A and the hollow fiber membrane bundle 3B are configured with multiple hollow fiber membranes 31. Although the purposes of use of the hollow fiber membrane bundle 3A and the hollow fiber membrane bundle 3B are different from each other, the same hollow fiber membranes 31 may be used, for example. Hereinafter, the hollow fiber membrane bundle 3B used for heat exchange will be representatively described.

As illustrated in FIG. 7, the winding path taken by the hollow fiber membrane 31 as it progresses between opposite ends of membrane bundle 3B is tilted with respect to a central axis O of the first cylinder member 241 (cylinder body), which is the core thereof, and is wound around the central axis O. A tilt angle (lead angle) θ of this hollow fiber membrane 31 with respect to the central axis O ranges from 22° to smaller than 67°, preferably ranges from 22° to smaller than 61°, and more preferably ranges from 26° to smaller than 57°. A further preferable range of the numerical value for the tilt angle (lead angle) θ of the hollow fiber membrane 31 with respect to the central axis O is a range from 46° to 50° corresponding to Example 2 among examples described below. According to the range of the numerical value described above, a length L2 from a right end opening 318 to a left end opening 319 of the hollow fiber membrane 31 can be shortened to an extent that the heat exchange function per one hollow fiber membrane 31 is not impaired. Note that, the right end opening 318 is an inlet port through which the heat medium H flows into the hollow fiber membrane 31, and the left end opening 319 is an outlet port through which the heat medium H flows out from the inside of the hollow fiber membrane 31. Since the length L2 is shortened as tilt angle θ is reduced (as compared to prior art winding methods), a pressure loss of the heat medium H passing through the hollow fiber membrane 31 can be prevented as much as possible. Accordingly, the hollow fiber membrane bundle 3B (the heat exchange section 10B) can smoothly and promptly perform heat exchange with respect to the blood B, thereby having an excellent heat exchange rate. The blood B which has been subjected to heat exchange has a suitable temperature and is returned to a patient.

In addition, an increase in the filling amount of the blood B tends to be a burden on a patient. Since the outer diameter of each of the hollow fiber membranes 31 is reduced as much as possible, an increase in the filling amount of the blood B can be prevented. Thus, a burden on a patient can be reduced. Note that, the interval (i.e., gap) between the hollow fiber membranes 31 preferably ranges from 1/10 to 1/1 of an outer diameter $\phi d_2$ of the hollow fiber membrane 31.

An inner diameter $\phi d_1$ of the hollow fiber membrane 31 preferably ranges from 0.2 mm to 0.9 mm and more preferably ranges from 0.35 mm to 0.75 mm (refer to FIG. 6). The outer diameter $\phi d_2$ of the hollow fiber membrane 31 preferably ranges from 0.3 mm to 1 mm and more preferably ranges from 0.45 mm to 0.85 mm (refer to FIG. 6). When the inner diameter $\phi d_1$ and the outer diameter $\phi d_2$ are within such ranges of the numerical value, the hollow fiber membrane 31 can retain its own strength, and a pressure loss of the heat medium H can be more reliably prevented due to the synergistic effect with the short length L2.

The constituent material of the hollow fiber membrane 31 is a resin material having a predetermined Young's modulus E. The Young's modulus E is 2.6 GPa or smaller, preferably ranges from 0.07 GPa to 1.6 GPa, and more preferably ranges from 0.24 GPa to 1.3 GPa. The resin material having such a Young's modulus E is not particularly limited. Examples thereof include thermoplastic resins. Among these, particularly, polyamide (for example: nylon 6, nylon 46, nylon 66, nylon 610, nylon 612, nylon 11, nylon 12, nylon 6-12, or nylon 6-66), a polyamide-based thermoplastic elastomer, and other various thermoplastic elastomers such as a polyester-based thermoplastic elastomer are preferably used. Since the hollow fiber membrane 31 is configured with such a material, when the hollow fiber membrane 31 is in a pulled state during a process of manufacturing the oxygenator 10 described below, the hollow fiber membrane 31 is stretched and the inner diameter $\phi d_1$ is accordingly reduced. However, the degree of diameter reduction can be prevented from being excessive, that is, the hollow fiber membrane 31 can be prevented from being squashed and blocking the flow path 32. Accordingly, the heat medium H can smoothly pass through the inside of the hollow fiber membrane 31, thereby preventing an excessive pressure loss.

In addition, the method of manufacturing the hollow fiber membrane 31 is not particularly limited. Examples thereof include a method of using extrusion molding, and other methods such as a stretching method and a solid and liquid phase separation method.

The hollow fiber membrane bundle 3B is obtained from a base material 3' in which such multiple hollow fiber membranes 31 are integrated and are wound to exhibit a shape of a cylinder body as a whole shape. This base material 3' is manufactured by the "method of manufacturing a heat exchanger" of the present invention. In addition, steps of this manufacturing method are included in the method of manufacturing the oxygenator 10. Accordingly, the method of manufacturing the oxygenator 10 includes steps to an extent that the oxygenator 10 is completed, such that not only the hollow fiber membrane bundle 3B is manufactured but also the hollow fiber membrane bundle 3A is manufactured thereafter. As the steps thereof, there are a first step, a second step, a third step, a fourth step, a fifth step, and a sixth step. Next, the first step to the sixth step will be described.

First Step

The first step is a winding step of winding each of the hollow fiber membranes 31 around the central axis O while the path of the hollow fiber membrane 31 is tilted with respect to the central axis O in the pulled state of being pulled in a longitudinal direction. Accordingly, the base material (primary base material) 3' is obtained.

In this first step, a winding apparatus 60 illustrated in FIGS. 8 and 9 is preferably used. The winding apparatus 60 includes tubular core rotary means 601, a winding device 602, and a fixing device 600.

The tubular core rotary means 601 is provided with a motor 603, a motor shaft 604, and a core attachment member 605 which is fixed to the motor shaft 604. The first cylinder member 241 which is a part of the housing 2A of the oxygenator 10 is attached to the core attachment member 605 and is rotated by the motor 603.

The winding device 602 is provided with a main body portion 606 including an accommodation portion which internally accommodates the hollow fiber membrane 31, and a discharge portion 705 discharging the hollow fiber membrane 31 and moving in an axial direction (arrow M1 direction in FIG. 8) of the main body portion 606. Moreover, the main body portion 606 is fixed to a linear table 608 and a ball nut member 704 moving on a linear rail 607. When a motor 703 is driven and a ball screw shaft 609 rotates, the ball nut member 704 can move in a manner parallel to the axial direction of the main body portion 606. The motor 703 can rotate normally and reversely and a controller (not illustrated) adjusts the driving thereof.

The fixing device 600 is a device fixing the hollow fiber membrane 31 wound around the first cylinder member 241, using fixing strings (string-like bodies) 11. The fixing device 600 includes a first feeding mechanism 701A disposed on the right side, a second feeding mechanism 701B disposed on the left side, and a discharging mechanism 702.

The first feeding mechanism 701A is a mechanism feeding the fixing string 11 to the right end side in FIG. 8 (the same applies to FIG. 9) with respect to the discharging mechanism 702. In addition, the second feeding mechanism 701B is a mechanism feeding the fixing string 11 to the left end side in FIG. 8 with respect to the discharging mechanism 702. The first feeding mechanism 701A and the second feeding mechanism 701B have the same configuration except that disposed locations are different from each other. Therefore, hereinafter, the first feeding mechanism 701A will be representatively described.

The first feeding mechanism 701A has a support portion 708 rotatably supporting a bobbin 113 around which the fixing string 11 is wound in advance, a tensioner 709 applying a tensile force to the fixing string 11, a coil spring 801 biasing the tensioner 709, and a detection sensor 802 detecting the presence or absence of the fixing string 11.

The support portion 708 is disposed on the farthest upstream side in a transportation direction of the fixing string 11. Note that, the support portion 708 may rotate with the bobbin 113 or may be fixed.

The tensioner 709 is a roller disposed downstream in the transportation direction of the fixing string 11 with respect to the support portion 708. A tensile force can be applied to the fixing string 11 by winding a middle part of the fixing string 11 around the tensioner 709.

The coil spring 801 can bias a central portion of the tensioner 709 along the central axis direction thereof. The fixing string 11 oscillates while being fed and is likely to be loosened. However, the coil spring 801 biases the fixing string 11 together with the tensioner 709, so that a tensile force is reliably applied regardless of the degree of the oscillation thereof.

The detection sensor 802 is a sensor disposed downstream in the transportation direction of the fixing string 11 with respect to the tensioner 709, that is, disposed between the tensioner 709 and the discharging mechanism 702. The detection sensor 802 is not particularly limited. For example, a force sensor or the like can be used. For example, in a case where the fixing string 11 runs out or is unintentionally cut while fixing the hollow fiber membrane 31, this detection sensor 802 can reliably detect the state thereof.

The discharging mechanism 702 is a mechanism independently discharging the fixing string 11 fed from the first feeding mechanism 701A, and the fixing string 11 fed from the second feeding mechanism 701B toward the first cylinder member 241 on the core attachment member 605. The discharging mechanism 702 has a main body portion 706 individually pulling out (feeding) each of the fixing strings 11, and a discharge portion 707 individually discharging the fixing strings 11 toward both end portions of the first cylinder member 241. When the hollow fiber membrane 31 is fixed by using the fixing strings 11, the fixing strings 11 discharged from the discharge portion 707 are wound around the hollow fiber membrane 31 on the rotating first cylinder member 241, and the hollow fiber membrane 31 is fixed (refer to FIG. 13). After the hollow fiber membrane 31 is fixed, the fixing string 11 adopted for the fixing is cut off from the fixing device 600 by using scissors or a cutter (not illustrated), for example. A cut portion of the fixing string 11 is fixed by using an adhesive tape or performing ultrasound welding, for example. Note that, the winding apparatus 60 is configured to be used without cutting the fixing string 11 until manufacturing of the hollow fiber membrane bundle 3B is completed.

In addition, as illustrated in FIG. 9, in the winding apparatus 60, the first cylinder member 241 on the core attachment member 605 can move along a central axis O direction (arrow M2), so that the discharging mechanism 702 can move along the central axis O direction (arrow M3) by being interlocked (synchronized) with the movement thereof. Due to such a configuration, the base material 3' (the hollow fiber membrane bundle 3B) in its entirety in the process of being manufactured can move along the central axis O direction, and the fixing string 11 can follow the movement thereof. Note that, in the winding apparatus 60, movement in the arrow M2 direction and the arrow M3 direction is independent from the movement in the arrow M1 direction.

As the constituent material of the fixing string 11, for example, the same resin material as that of the hollow fiber membrane 31 may be used, or other metal materials such as stainless steel may be used. In addition, the fixing string 11 is preferably configured with a belt-like body having a flat cross-sectional shape as illustrated in FIG. 13. However, the cross-sectional shape thereof is not limited. For example, the fixing string 11 may be configured with a string-like body having a circular cross-sectional shape.

The first step is performed by using the winding apparatus 60 having a configuration as described above. Hereinafter, one hollow fiber membrane 31 will be representatively described.

In the first step, the hollow fiber membrane 31 is reciprocated in the central axis O direction, that is, a transverse direction while being wound around the central axis O of the first cylinder member 241 (the cylinder body) on the outer peripheral portion of the first cylinder member 241. At this time, as an example, as illustrated in FIG. 10, the hollow fiber membrane 31 starts to be wound from a start point 311 on the left side and is directed toward the right side. On the right side, the hollow fiber membrane 31 is turned back at a turning point (turned-back portion) 312. Thereafter, the hollow fiber membrane 31 is sequentially turned back at a turning point (turned-back portion) 313 on the left side and a turning point (turned-back portion) 314 on the right side, thereby reaching an end point 315 on the left side. That is, in a winding form illustrated in FIG. 10, the hollow fiber membrane 31 is wound in the order of the arrows i→ii→iii→iv→v→vi→vii during a round trip around the central axis O. In the first step, the hollow fiber membranes 31 are layered in an overlapping manner while repeating such winding. Note that, there is no need to mention that the winding form of the hollow fiber membrane 31 is not limited to the winding form illustrated in FIG. 10. In any winding form, as described above, the tilt angle θ with respect to the central axis O of the hollow fiber membrane 31 ranges from 22° to 67°.

In addition, in the first step, the hollow fiber membrane 31 is wound in the pulled state of being pulled in the longitudinal direction. This pulled (i.e., stretched) state is maintained even in the completed oxygenator 10 because the fixing strings or bands holding opposite ends of membrane 31 near consecutive turning points maintains the tension created during the first step (and is later maintained by potting of the ends as described below). The stretching rate of the hollow fiber membrane 31 in the pulled state ranges from 0.5% to 3% and preferably ranges from 0.5% to 1%. Due to such winding, in any case of manufacturing the oxygenator 10 (winding the hollow fiber membrane 31) and using the oxygenator 10, the hollow fiber membrane 31 can be prevented from being loosened, and the interval between the hollow fiber membranes 31 can be reliably prevented from being not uniform. Note that, the "stretching rate" indicates a value obtained from $((Q_b-Q_a)/Q_a) \times 100$ when the length of the hollow fiber membrane 31 in a natural state (refer to FIG. 11(*a*)) where no external force is applied is $Q_a$, and the length of the hollow fiber membrane 31 when the hollow fiber membrane 31 is stretched (refer to FIG. 11(*b*)) from the natural state by applying a pulling force F1 is $Q_b$. In addition, the pulling force F1 preferably ranges from 0.1 N to 5 N and more preferably ranges from 0.1 N to 1.5 N.

In addition, the hollow fiber membrane 31 is tilted at the tilt angle θ with respect to the central axis O in the pulled state. Therefore, if the tilt angle θ becomes small, the hollow fiber membrane 31 needs to be fixed at the turning point 312, the turning point 313, and the turning point 314 individually formed on the right and left sides of the hollow fiber membrane 31. Hereinafter, fixing at the turning point 312 will be representatively described.

As illustrated in FIG. 13, every time the hollow fiber membrane 31 is turned back at the turning point 312, a spot in the vicinity of the turning point 312 is fixed. This fixing is performed by causing the fixing string 11 supplied from the fixing device 600 of the winding apparatus 60 to be wound around the central axis O and to be overlapped in the vicinity of the turning point 312. Accordingly, the hollow fiber membrane 31 can form the turning point 312 and can be reliably turned back regardless of the size of the tilt angle θ. The hollow fiber membrane 31 is precisely wound while the pulled state is maintained. Accordingly, the interval between the hollow fiber membranes 31 can be reliably and uniformly maintained (since each individual strand of membranes 31 is under tension and maintains a straight path between the fixing points). Thus, a flow inside the heat exchange section 10B (heat exchange layer) becomes uniform, thereby realizing the heat exchange section 10B (heat exchanger) having an excellent heat exchange rate. Note that, as described below, this fixing string 11 remains in the base material 3' without any change but is removed in the hollow fiber membrane bundle 3B.

As described above, a tensile force is applied to the fixing string 11 by the tensioner 709. Accordingly, the fixing string 11 can be fixed such that the hollow fiber membrane 31 is fastened toward the central axis O side. At this time, a static friction force F2 between the hollow fiber membrane 31 and the first cylinder member 241 is greater than the pulling force F1. Accordingly, the hollow fiber membrane 31 can be reliably fixed via the fixing string 11. Note that, for example, a tensile force acting on the fixing string 11 by the tensioner 709 preferably ranges from 0.1 N to 10 N and more preferably ranges from 0.1 N to 3 N.

Second Step

The second step is a winding step of further winding the hollow fiber membrane 31, which becomes the hollow fiber membrane bundle 3A, on the base material 3'. Accordingly, a secondary base material 3" as illustrated in FIG. 12A is obtained.

In this second step, the winding apparatus 60 is used without any change. For example, the hollow fiber membrane 31 can be wound in a winding form similar to that of the first step. After the second step is completed, the secondary base material 3" is taken out from the winding apparatus 60 together with the first cylinder member 241.

Third Step

The third step is an accommodation step of accommodating the secondary base material 3" in the cylindrical housing main body 21A together with the first cylinder member 241 after the filter member 41A is fixedly wound around the secondary base material 3".

Fourth Step

The fourth step is a fixing step of fixing the secondary base material 3" to the cylindrical housing main body 21A. The secondary base material 3" is fixed by using a potting material 50, and the potting material 50 becomes the partition wall 8 and the partition wall 9.

In order to perform this fixing, a liquid polyurethane which is the constituent material of the potting material 50 is firstly supplied toward both end portions of the secondary base material 3" inside the cylindrical housing main body 21A. Subsequently, the cylindrical housing main body 21A in its entirety is mounted in a centrifugal separator. Thereafter, the liquid polyurethane is dried. Accordingly, both end portions of the secondary base material 3" are in a state of being fixed by the potting material 50 (refer to FIG. 12A). Note that, both end portions of the secondary base material 3" also include the turning point 312, the turning point 313, the turning point 314, the start point 311, and the end point 315 fixed by using the fixing string 11 in the first step.

Fifth Step

As illustrated in FIGS. 12A and 12B, the fifth step is a cutting step of individually cutting both end portions of the secondary base material 3" fixed by the potting material 50. Accordingly, it is possible to collectively obtain the hollow fiber membrane bundle 3A and the hollow fiber membrane bundle 3B which can be used in the oxygenator 10.

In this fifth step, a cutting apparatus 90 illustrated in FIG. 12A is used. The cutting apparatus 90 has two cutters (edged tools) 901. When each of the cutters 901 approaches the secondary base material 3", both end portions of the secondary base material 3" are cut. Note that, the cutting apparatus 90 is not limited to an apparatus configured to have the cutters 901. For example, an apparatus configured to jet a water jet or an apparatus configured to emit a laser beam may be adopted.

As illustrated in FIG. 12A, in the left end portion of the part fixed by the potting material 50 of the secondary base material 3", a first cut line 351 is set in a part closer to the right side than the fixing string 11. In the right end portion as well, a second cut line 352 is set in a part closer to the left side than the fixing string 11.

The secondary base material 3" is cut along the first cut line 351 and the second cut line 352 by using the cutters 901 of the cutting apparatus 90. Accordingly, as illustrated in FIG. 12B, the secondary base material 3" is divided into three members, and the member positioned at the center becomes the hollow fiber membrane bundle 3A and the hollow fiber membrane bundle 3B. Note that, the members at both ends are discarded.

In addition, due to this cutting, in the hollow fiber membrane bundle 3B (the same applies to the hollow fiber membrane bundle 3A), the turning point 312, the turning point 313, and the turning point 314 are removed together with the fixing string 11. Accordingly, the right end opening 318 open to the right end side is formed in an open manner in each of the hollow fiber membranes 31 constituting the hollow fiber membrane bundle 3B, and the left end opening 319 is formed on the left end side. Accordingly, the heat medium H can pass through the inside of the hollow fiber membrane 31. Note that, in the hollow fiber membrane bundle 3A, the gas G passes through the inside of each of the hollow fiber membranes 31.

Sixth Step

The sixth step is a mounting step of mounting each of the first lid 22A and the second lid 23A in the cylindrical housing main body 21A. Note that, after this mounting, for example, each of the first lid 22A and the second lid 23A may be fixed to the cylindrical housing main body 21A using an adhesive or the like.

The oxygenator 10 with a heat exchanger can be obtained by going through the first step to the sixth step in order as described above.

Second Embodiment

Figure 14:
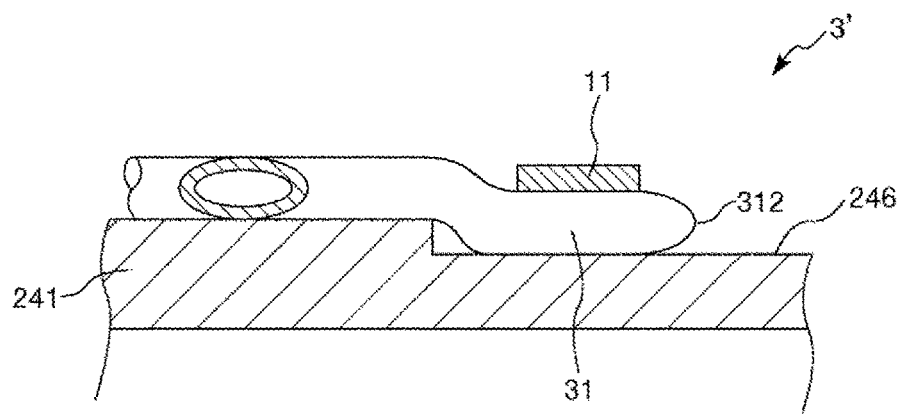
FIG. 14 is a cross-sectional view illustrating a fixed state of the hollow fiber membrane during a process of manufacturing a heat exchanger according to a second embodiment.

FIG. 14 is a cross-sectional view illustrating a fixed state of the hollow fiber membrane during a process of manufacturing a heat exchanger (second embodiment).

Hereinafter, with reference to FIG. 14, a second embodiment of a heat exchanger, an oxygenator, and a method of manufacturing a heat exchanger according to the present invention will be described. However, description will be given while focusing on points different from those of the aforementioned embodiment, and description of similar items will be omitted.

The present embodiment is similar to the first embodiment except for the difference in the shape of the first cylinder member that is a core around which the hollow fiber membrane is wound.

As illustrated in FIG. 14, in the present embodiment, a stepped portion 246 is formed in the right end portion of the outer peripheral portion of the first cylinder member 241. The stepped portion 246 is a part in which the outer diameter of the first cylinder member 241 is reduced, and which is formed along the circumferential direction of the outer peripheral portion of the first cylinder member 241. Note that, the difference of elevation between the stepped portion 246 and a part closer to the left side than the stepped portion 246 is preferably equal to or smaller than the outer diameter φd₂ of the hollow fiber membrane 31. In addition, in the diagram, the stepped portion 246 on the right end portion side is depicted. However, similarly, the stepped portion 246 is protrusively formed on the left end portion side as well.

The turning point 312 of the hollow fiber membrane 31 is disposed on the stepped portion 246, and the fixing string 11 is also disposed on the stepped portion 246. Accordingly, the hollow fiber membrane 31 can be rapidly deformed at a boundary portion between the stepped portion 246 and a part closer to the left side than the stepped portion 246 and can engage with the boundary portion. Due to this engagement, the hollow fiber membrane 31 is firmly fixed, and the hollow fiber membrane 31 can be wound while the pulled state with respect to the hollow fiber membrane 31 is maintained. Thus, the interval between the hollow fiber membranes 31 can be more reliably and uniformly maintained.

Third Embodiment

Figure 15:
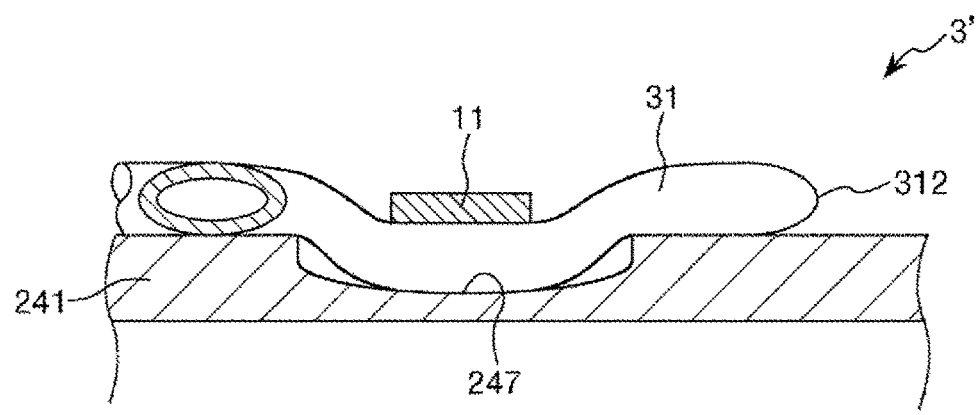
FIG. 15 is a cross-sectional view illustrating the fixed state of the hollow fiber membrane during a process of manufacturing a heat exchanger according to a third embodiment.

FIG. 15 is a cross-sectional view illustrating the fixed state of the hollow fiber membrane during a process of manufacturing a heat exchanger (third embodiment).

Hereinafter, with reference to FIG. 15, a third embodiment of a heat exchanger, an oxygenator, and a method of manufacturing a heat exchanger according to the present invention will be described. However, description will be given while focusing on points different from those of the aforementioned embodiments, and description of similar items will be omitted.

The present embodiment is similar to the first embodiment except for the difference in the shape of the first cylinder member that is a core around which the hollow fiber membrane is wound.

As illustrated in FIG. 15, in the present embodiment, a recessed groove 247 is formed in the right end portion of the outer peripheral portion of the first cylinder member 241. The groove 247 is formed along the circumferential direction of the outer peripheral portion of the first cylinder member 241. Note that, the depth of the groove 247 is preferably equal to or smaller than the outer diameter φd₂ of the hollow fiber membrane 31. The width of the groove 247 is preferably equal to or greater than the width of the fixing string 11. In addition, in the diagram, the groove 247 on the right end portion side is depicted. However, similarly, the groove 247 is also formed on the left end portion side.

The turning point 312 of the hollow fiber membrane 31 is disposed closer to the right side than the groove 247. In addition, the fixing string 11 is disposed to overlap the groove 247 when the fixing string 11 is viewed from the outer peripheral portion side of the first cylinder member 241 (upper side in FIG. 15). Due to such a positional relationship, the hollow fiber membrane 31 enters the groove 247, so that the hollow fiber membrane 31 can be firmly fixed. Accordingly, the hollow fiber membrane 31 can be wound while the pulled state with respect to the hollow fiber membrane 31 is maintained. Thus, the interval between the hollow fiber membranes 31 can be more reliably and uniformly maintained.

Hereinabove, the embodiments of the heat exchanger, the oxygenator, and the method of manufacturing a heat exchanger of the present invention have been described based on the drawings. The present invention is not limited thereto. Each of the sections constituting the heat exchanger and the oxygenator can be replaced with a section having any configuration which can exhibit a similar function. In addition, any constituent material may be added.

In addition, the heat exchanger, the oxygenator, and the method of manufacturing a heat exchanger of the present invention may be realized by combining any of two or more configurations (features) from each of the embodiments described above.

In addition, each of the hollow fiber membranes constituting the hollow fiber membrane bundle of the oxygenator section and each of the hollow fiber membranes constituting the hollow fiber membrane bundle of the heat exchange section are the same as each other in each of the embodiments described above. However, the configuration is not limited thereto. For example, one (former) hollow fiber membrane may be thinner than the other (latter) hollow fiber membrane, or both hollow fiber membranes may be configured with materials different from each other.

In addition, in the oxygenator section and the heat exchange section, the heat exchange section is disposed inside and the oxygenator section is disposed outside in each of the embodiments described above. However, the configuration is not limited thereto. The oxygenator section may be disposed inside and the heat exchange section may be disposed outside. In this case, blood flows from the outside toward the inside.

In addition, in each of the embodiments described above, a case where the heat exchanger of the present invention is applied to an oxygenator has been described as an example. However, the application is not limited thereto.

EXAMPLES

Hereinafter, specific examples of the present invention will be described. Note that, the present invention is not limited thereto.

Preparation of Heat Exchange Section for Oxygenator

Example 1

A heat exchange section for an oxygenator illustrated in FIGS. 1 to 5 was prepared. In this heat exchange section for an oxygenator, the housing was formed of polycarbonate. The inside dimension of the housing was φ90×80 mm.

The tilt angle θ of the hollow fiber membrane, the Young's modulus E of the hollow fiber membrane, the constituent material of the hollow fiber membrane, the stretching rate of the hollow fiber membrane, the inner diameter φd₁ of the hollow fiber membrane in a natural state, the outer diameter φd₂ of the hollow fiber membrane in a natural state, the length L2 per one hollow fiber membrane positioned at a layer on the innermost side in the hollow fiber membrane bundle, the interval between the hollow fiber membranes positioned at the layer on the innermost side in the hollow fiber membrane bundle, and the area of the outer surface of the hollow fiber membrane bundle were set as shown in Table 1.

Example 2

The tilt angle θ of the hollow fiber membrane, the Young's modulus E of the hollow fiber membrane, the constituent material of the hollow fiber membrane, the stretching rate of the hollow fiber membrane, the inner diameter φd₁ of the hollow fiber membrane in a natural state, the outer diameter φd₂ of the hollow fiber membrane in a natural state, the length L2 per one hollow fiber membrane positioned at a layer on the innermost side in the hollow fiber membrane bundle, the interval between the hollow fiber membranes positioned at the layer on the innermost side in the hollow fiber membrane bundle, and the area of the outer surface of the hollow fiber membrane bundle were set as shown in Table 1. For the rest, configurations similar to those of Example 1 were applied, and a heat exchange section for an oxygenator of Example 2 was obtained.

Example 3

The tilt angle θ of the hollow fiber membrane, the Young's modulus E of the hollow fiber membrane, the constituent material of the hollow fiber membrane, the stretching rate of the hollow fiber membrane, the inner diameter φd$_1$ of the hollow fiber membrane in a natural state, the outer diameter φd$_2$ of the hollow fiber membrane in a natural state, the length L2 per one hollow fiber membrane positioned at a layer on the innermost side in the hollow fiber membrane bundle, the interval between the hollow fiber membranes positioned at the layer on the innermost side in the hollow fiber membrane bundle, and the area of the outer surface of the hollow fiber membrane bundle were set as shown in Table 1. For the rest, configurations similar to those of Example 1 were applied, and a heat exchange section for an oxygenator of Example 3 was obtained.

Example 4

The tilt angle θ of the hollow fiber membrane, the Young's modulus E of the hollow fiber membrane, the constituent material of the hollow fiber membrane, the stretching rate of the hollow fiber membrane, the inner diameter φd$_1$ of the hollow fiber membrane in a natural state, the outer diameter φd$_2$ of the hollow fiber membrane in a natural state, the length L2 per one hollow fiber membrane positioned at a layer on the innermost side in the hollow fiber membrane bundle, the interval between the hollow fiber membranes positioned at the layer on the innermost side in the hollow fiber membrane bundle, and the area of the outer surface of the hollow fiber membrane bundle were set as shown in Table 1. For the rest, configurations similar to those of Example 1 were applied, and a heat exchange section for an oxygenator of Example 4 was obtained.

Comparative Example 1

The tilt angle θ of the hollow fiber membrane, the Young's modulus E of the hollow fiber membrane, the constituent material of the hollow fiber membrane, the stretching rate of the hollow fiber membrane, the inner diameter φd$_1$ of the hollow fiber membrane in a natural state, the outer diameter φd$_2$ of the hollow fiber membrane in a natural state, the length L2 per one hollow fiber membrane positioned at a layer on the innermost side in the hollow fiber membrane bundle, the interval between the hollow fiber membranes positioned at the layer on the innermost side in the hollow fiber membrane bundle, and the area of the outer surface of the hollow fiber membrane bundle were set as shown in Table 1. For the rest, configurations similar to those of Example 1 were applied, and a heat exchange section for an oxygenator of Comparative Example 1 corresponding to known prior art was obtained.

Evaluation

In a simulative usage state, with respect to the heat exchange sections for an oxygenator of Examples 1 to 4 and Comparative Example 1, the (maximum) pressure loss of water in the hollow fiber membrane bundle, the (maximum) filling amount of blood filling the inside of the heat exchange section for an oxygenator, and the heat exchange rate were measured.

The "pressure loss of water" was measured by using water at 40° C., when the water was caused to flow 15 L per minute. The amount of water flowed for one minute was postulated based on the maximum flow rate of the oxygenator in actual use. In addition, the "heat exchange rate" was measured when the amount of blood flowed for one minute was 4 L. The amount of blood flowed for one minute was postulated based on a blood flow rate which is very frequently used for oxygenators.

Moreover, with respect to the heat exchange sections for an oxygenator of Examples 1 to 4 and Comparative Example 1, whether or not each of the heat exchange sections for an oxygenator is suitable for actual use is generally evaluated in accordance with the following evaluation criterion 1.

Evaluation Criterion 1 are defined according to the following categories:

A: remarkably excellent compared to the existing heat exchange sections for an oxygenator.
B: excellent compared to the existing heat exchange sections for an oxygenator.
C: slightly excellent compared to the existing heat exchange sections for an oxygenator.
D: equal to or poor compared to the existing heat exchange sections for an oxygenator.

The evaluation result 1 thereof is included in Table 1. Note that, as the reason that the item of the "tilt angle θ of the hollow fiber membrane" in Table 1 varies in Examples 1 to 4 and Comparative Example 1, the tilt angle θ tends to be increased as the number of times the hollow fiber membranes are wound increase.

TABLE 1

| | Example 1 | Example 2 | Example 3 | Example 4 | Comparative Example 1 |
|---|---|---|---|---|---|
| Tilt angle (lead angle) θ of hollow fiber membrane [°] | 22 to 25 | 46 to 50 | 58 to 61 | 65 to 67 | 69 to 71 |
| Young's modulus E of hollow fiber membrane [GPa] | 0.24 | 0.24 | 0.24 | 0.24 | 0.24 |
| Constituent material of hollow fiber membrane | Polyester elastomer | Polyester elastomer | Polyester elastomer | Polyester elastomer | Polyester elastomer |
| Stretching rate of hollow fiber membrane [%] | 1 | 1 | 1 | 1 | 1 |
| Inner diameter φd1 of hollow fiber membrane in natural state [mm] | 0.45 | 0.45 | 0.45 | 0.45 | 0.45 |
| Outer diameter φd2 of hollow fiber membrane in natural state [mm] | 0.55 | 0.55 | 0.55 | 0.55 | 0.55 |

TABLE 1-continued

|  | Example 1 | Example 2 | Example 3 | Example 4 | Comparative Example 1 |
|---|---|---|---|---|---|
| Length L2 per one hollow fiber membrane positioned at layer on innermost side in hollow fiber membrane bundle [mm] | 87 | 116 | 150 | 187 | 226 |
| Interval between hollow fiber membranes positioned at layer on innermost side in hollow fiber membrane bundle [μm] | 50 | 50 | 50 | 50 | 50 |
| Area of outer surface of hollow fiber membrane bundle [m2] | 0.45 | 0.45 | 0.45 | 0.45 | 0.45 |
| Pressure loss of water [mmHg] | 26 | 47 | 79 | 124 | 181 |
| Blood filling amount [mL] | 32 | 27 | 27 | 26 | 26 |
| Heat exchange rate | 0.74 | 0.74 | 0.74 | 0.74 | 0.74 |
| Evaluation | B | A | B | C | D |

As is clear from Table 1, among Examples 1 to 4, the heat exchange section for an oxygenator of Example 2 is remarkably suitable for actual use, the heat exchange sections for an oxygenator of Examples 1 and 3 are subsequently suitable for actual use, and then the heat exchange section for an oxygenator of Example 4 is suitable for actual use, as a result.

In addition, in the description above, the present invention has been described with reference to favorable embodiments. However, the present invention is not limited to each of the embodiments described above. Various modifications and changes can be made without departing from the gist and the scope of the present invention.

A heat exchanger of the present invention is a heat exchanger including multiple hollow fiber membranes that each have a hollow portion through which a heat medium passes, and exhibiting a shape of a cylinder body as a whole shape in which the multiple hollow fiber membranes are integrated. Each of the hollow fiber membranes is tilted with respect to a central axis of the cylinder body and is wound around the central axis of the cylinder body. A tilt angle θ with respect to the central axis of the cylinder body of each of the hollow fiber membranes ranges from 22° to smaller than 67°. A constituent material of each of the hollow fiber membranes has a Young's modulus E of 2.6 GPa or smaller. Therefore, a pressure loss of the heat medium passing through each of the hollow fiber membranes can be prevented as much as possible and reduction of a filling amount of liquid (for example, blood) which is a target of heat exchange inside the heat exchanger can be achieved.

What is claimed is:

1. A heat exchanger for an oxygenator, comprising:
   a cylinder member;
   multiple hollow fiber membranes that each have a hollow portion through which a heat medium passes, and exhibiting a shape of a cylinder body as a whole shape in which the multiple hollow fiber membranes are each wound onto the cylinder member along a path which is tilted with respect to a central axis of the cylinder according to a tilt angle θ with respect to the central axis of the cylinder member which ranges from 22° to smaller than 67°, and wherein a constituent material of each of the hollow fiber membranes has a Young's modulus E of 2.6 GPa or smaller; and
   fixing bodies at opposing sides of the cylinder member fixing opposite ends of each of the hollow fiber membranes such that each hollow fiber membrane is fixed under tension that stretches each hollow fiber membrane at a stretching rate between 0.5% and 3.0%, wherein stretching of the hollow fiber membranes reduces an outer diameter of the hollow fiber membranes and a blood filling amount of the heat exchanger is accordingly reduced.

2. The heat exchanger according to claim 1, wherein the Young's modulus E is 0.07 GPa or greater.

3. The heat exchanger according to claim 1, wherein the constituent material of each of the hollow fiber membranes is a polyamide-based resin material or a polyester-based resin material.

4. The heat exchanger according to claim 1, wherein each hollow fiber membrane has an outer diameter of 1 mm or smaller in a natural state without stretching.

5. The heat exchanger according to claim 1, wherein the fixing bodies are comprised of potting material applied over the respective ends of the hollow fiber membranes.

6. The heat exchanger according to claim 1, wherein the stretching rate is between 0.5% and 1.0%.

7. A method of manufacturing a heat exchanger including multiple hollow fiber membranes that each have a hollow portion through which a heat medium passes, and exhibiting a shape of a cylinder body as a whole shape disposed over a cylinder member, the method comprising:
   winding each of the hollow fiber membranes around a central axis of the cylinder following a path which is tilted at a tilt angle θ with respect to the central axis of the cylinder body while simultaneously tensioning the hollow fiber membranes in a pulled state wherein the hollow fiber membrane is stretched in a longitudinal direction of the hollow fiber membrane at a stretching rate of each of the hollow fiber membranes ranging from 0.5% to 3%, wherein tilt angle θ with respect to the central axis of the cylinder body of each of the hollow fiber membranes ranges from 22° to smaller than 67°, and wherein a constituent material of each of the hollow fiber membranes has a Young's modulus E of 2.6 GPa or smaller; and
   fixing the hollow fiber membranes as opposing ends of the cylinder member to maintain the stretching of the hollow fiber membranes.

8. The method of manufacturing a heat exchanger according to claim 7,
wherein the Young's modulus E is 0.07 GPa or greater.

9. The method of manufacturing a heat exchanger according to claim 7,
wherein the constituent material of each of the hollow fiber membranes is a polyamide-based resin material or a polyester-based resin material.

10. The method of manufacturing a heat exchanger according to claim 7,
wherein the hollow fiber membrane has an outer diameter of 1 mm or smaller in a natural state without stretching.

11. The method of manufacturing a heat exchanger according to claim 7,
wherein in the winding step, each of the hollow fiber membranes is wound by reciprocating each of the hollow fiber membranes on an outer peripheral portion of the cylinder member in a central axis direction; and
wherein in the winding step, when each of the hollow fiber membranes is reciprocating, a turned-back portion is formed by causing the hollow fiber membrane to be turned back on both one end and the other end of the cylinder member, and the fixing step is comprised of winding a fixing string around the central axis of the cylinder member in the vicinity of the turned-back portion in an overlapping manner.

12. The method of manufacturing a heat exchanger according to claim 11,
wherein a stepped portion having a reduced outer diameter is formed at both ends of the cylinder member; and
wherein the fixing string is disposed in a manner overlapping the stepped portions at both the ends.

13. The method of manufacturing a heat exchanger according to claim 11,
wherein respective grooves are formed along a circumferential direction recessed from both the ends of the cylinder member; and
wherein the fixing string is disposed in a manner overlapping the grooves at both the ends.

14. The method of manufacturing a heat exchanger according to claim 7,
wherein the stretching rate is between 0.5% and 1.0%.

15. A gas exchanger for an oxygenator, comprising:
a cylinder member;
multiple hollow fiber membranes that each have a hollow portion through which a gas passes, and exhibiting a shape of a cylinder body as a whole shape in which the multiple hollow fiber membranes are each wound onto the cylinder member along a path which is tilted with respect to a central axis of the cylinder according to a tilt angle θ with respect to the central axis of the cylinder member which ranges from 22° to smaller than 67°, and wherein a constituent material of each of the hollow fiber membranes has a Young's modulus E between 0.07 GPa and 2.6 GPa; and
fixing bodies at opposing sides of the cylinder member fixing opposite ends of each of the hollow fiber membranes such that each hollow fiber membrane is fixed under tension that stretches each hollow fiber membrane at a stretching rate between 0.5% and 3.0%, wherein stretching of the hollow fiber membranes reduces an outer diameter of the hollow fiber membranes and a blood filling amount of the gas exchanger is accordingly reduced.

16. The gas exchanger according to claim 15,
wherein the constituent material of each of the hollow fiber membranes is a polyamide-based resin material or a polyester-based resin material, and wherein each hollow fiber membrane has an outer diameter of 1 mm or smaller in a natural state without stretching.

17. The gas exchanger according to claim 15,
wherein the fixing bodies are comprised of potting material applied over the respective ends of the hollow fiber membranes.

18. The gas exchanger according to claim 15,
wherein the stretching rate is between 0.5% and 1.0%.

* * * * *